(12) United States Patent
Koltin et al.

(10) Patent No.: US 6,251,593 B1
(45) Date of Patent: Jun. 26, 2001

(54) IDENTIFICATION OF EUKARYOTIC GROWTH-RELATED GENES AND PROMOTER ISOLATION VECTOR AND METHOD OF USE

(75) Inventors: Yigal Koltin, Newton; Perry Riggle, Norwood; Vicky Gavrias, Watertown; Chris Bulawa, Arlington, all of MA (US); Kenneth R. Winter, Seattle, WA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/084,346

(22) Filed: May 27, 1998

Related U.S. Application Data

(62) Division of application No. 09/004,225, filed on Jan. 8, 1998, now Pat. No. 6,020,133, which is a division of application No. 08/551,437, filed on Nov. 1, 1995, now Pat. No. 5,824,545.

(51) Int. Cl.[7] .............................. C12Q 1/68; C12N 1/14; C12N 15/63; C07H 21/04
(52) U.S. Cl. ................ 435/6; 435/254.22; 435/320.1; 536/24.1
(58) Field of Search ............................. 536/23.1, 23, 74, 536/24.1; 435/69.1, 7.21, 69.2, 69.9, 375, 320.1, 6, 254.22

(56) References Cited

U.S. PATENT DOCUMENTS

| | | | |
|---|---|---|---|
| 5,229,123 | 7/1993 | Masubuchi et al. | 424/408 |
| 5,434,065 | 7/1995 | Mahan et al. | 435/6 |

FOREIGN PATENT DOCUMENTS

PCT/US96/17459  11/1996  (WO).

OTHER PUBLICATIONS

Geber et al., Cloning and Characterization of a *Candida albicans* . . . , Journal of Bacteriology 174 (21) p 6992–6996, Nov. 1992.*

Au–Young et al., Isolation of a chitin sunthase . . . *Saccharomyces cerevisiae*, Molecular Microbiology, 4(2):197–207, 1990.

Bulawa et al., "Chitin synthase I and chitin synthase II are not required for chitin synthesis in vivo in *Saccharomyces cerevisiae*," *Proc. Natl., Acad. Sci. USA*, 87:7424–7428, 1990.

Bulawa et al., "Genetics and Molecular Biology of Chitin Synthesis in Fungi," *Annu. Rev. Microbiol.*, 47:505–534, 1993.

Choi et al., "The Use of Divalent . . . Yeast Chitin Synthetases," *Analytical Biochemistry*, 219:368–372, 1994.

Gold et al., "Disruption of two genes for chitin synthase in the phytopathogenic fungus *Ustilago maydis*," *Molecular Microbiology*, 11(5):897–902, 1994.

Mahan et al., "Selection of Bacterial Virulence Genes That Are Specifically Induced in Host Tissues," *Science* 259:686–688, 1993.

Myers et al., "Use of URA3 as a reporter of gene expression in *C. albicans*," *Curr Genet*, 27:243–248, 1995.

Shaw et al., "The Function of Chitin Synthases 2 and 3 in the *Saccharomyces cerevisiae* Cell Cycle," *The Journal of Cell Biology*, 114:111–123, 1991.

Valdes et al., "Antigens specific to pre–cysts . . . *Entamoeba invadens*," Abstract, Archivos de Investigacion Medica, 21:223–227, 1990.

Au–Young et al., Mol. Microbiol. 4, 2, 197–207, 1990.

Bulawa et al.,"The *S. cerevisiae* Structural Gene for Chitin Synthase is Not Required for Chitin Synthesis in Vivo," *Cell*, 1986.

Kang et al., "Isolation of Chitin Synthetase from *Saccharomyces cerevisiae*," *The Journal of Biological Chemistry*, 259:14966–14972, 1984.

\* cited by examiner

Primary Examiner—Remy Yuoel
Assistant Examiner—Lisa Gansheroff
(74) Attorney, Agent, or Firm—Fish & Richardson P.C.

(57) ABSTRACT

A polynucleotide encoding chitin synthase (CHS1), an enzyme essential for cell wall synthesis and yeast cell growth, is provided. A maltose responsive promoter (MRP) isolated using the promoter library of the invention is also described. The present invention also provides a vector for isolation of a eukaryotic regulatory polynucleotide, i.e., promoter. The vector is useful in the method of the invention which comprises identifying a eukaryotic regulatory polynucleotide, i.e., promoter region, by complementing the growth of an auxotrophic host cell containing the vector of the invention, which includes a promoter region operably linked to a promoterless auxotrophic gene. The vector is introduced into the host cell chromosome by targeted integration. Also provided is a library containing host cells having the vector of the invention integrated in the chromosome of the host cell.

8 Claims, 14 Drawing Sheets

```
                Alw21 I              Acc87 I
                AspH I               PflM I
                Bsi HKA I            PflM I
                HgiA I               Van91 I
ATGAAAAATATCGCTCATTTGTGCTCACGCCATAAATCCAAAATATGGGGCAAAGATAGCTGGAAAAAAGTTCAAGTGATAATTGTTGCA
————————————————————————————————————————————————————————————————————————————————————————— 1170
TACTTTTTATAGCGAGTAAACACGAGTGCGGTATTTAGGTTTTATACCCCGTTTCTATCGACCTTTTTTCAAGTTCACTATTAACAACGT
 M  K  N  I  A  H  L  C  S  R  H  K  S  K  I  W  G  K  D  S  W  K  K  V  Q  V  I  I  V  A
```

```
                                                                          Cfr I
                                                                          Eae I
                                                                           Bal I
                                                                           MluNI
                                                                           Msc I
                                                                           Msc I
                                                                            Dra II
                                                                 Acs I       Eco 0109 I   HinD II
                                  Bbv I                          Apo I       EcoO109 I    Hinc II
GATGGTAGAAATAAAGTTCAACAATCCGTTCTTGAATTGCTTACGGCAACAGGCTGCTATCAAGAAAATTTGGCCAGGCCCTATGTCAAC
————————————————————————————————————————————————————————————————————————————————————————— 1260
CTACCATCTTTATTTCAAGTTGTTAGGCAAGAACTTAACGAATGCCGTTGTCCGACGATAGTTCTTTTAAACCGGTCCGGGATACAGTTG
 D  G  R  N  K  V  Q  Q  S  V  L  E  L  L  T  A  T  G  C  Y  Q  E  N  L  A  R  P  Y  V  N
```

```
                                                        Acs I
                              Cla I                     Apo I
AATAGCAAAGTAAATGCCCATTTGTTTGAATATACCACTCAAATATCTATCGATGAGAACTTGAAATTCAAAGGAGATGAAAAAAACCTT
————————————————————————————————————————————————————————————————————————————————————————— 1350
TTATCGTTTCATTTACGGGTAAACAAACTTATATGGTGAGTTTATAGATAGCTACTCTTGAACTTTAAGTTTCCTCTACTTTTTTTGGAA
 N  S  K  V  N  A  H  L  F  E  Y  T  T  Q  I  S  I  D  E  N  L  K  F  K  G  D  E  K  N  L
```

```
 BseN I
 Bsr I
GCACCAGTTCAAGTCTTGTTCTGTTTGAAAGAACTGAACCAAAAGAAAATCAATTCCCATAGATGGCTTTTTAATGCCTTTTGTCCTGTC
————————————————————————————————————————————————————————————————————————————————————————— 1440
CGTGGTCAAGTTCAGAACAAGACAAACTTTCTTGACTTGGTTTTCTTTTAGTTAAGGGTATCTACCGAAAAATTACGGAAAACAGGACAG
 A  P  V  Q  V  L  F  C  L  K  E  L  N  Q  K  K  I  N  S  H  R  W  L  F  N  A  F  C  P  V
```

```
                            Acc65 I
                            Asp 718
                            Ban I                                    Asp 700
                            Bcg I*                                   BsaM I
                            HgiC I                                   Bsm I
                             Kpn I                          Bcg I    Xmn I
TTGGACCCCAATGTTATTGTTCTTTTAGATGTGGGTACCAAACCCGATAACCATGCCATTTATAATCTATGGAAAGCATTCGATAGAGAT
————————————————————————————————————————————————————————————————————————————————————————— 1530
AACCTGGGGTTACAATAACAAGAAAATCTACACCCATGGTTTGGGCTATTGGTACGGTAAATATTAGATACCTTTCGTAAGCTATCTCTA
 L  D  P  N  V  I  V  L  L  D  V  G  T  K  P  D  N  H  A  I  Y  N  L  W  K  A  F  D  R  D
```

```
                                                                                    Acs I
 Bbv I          Alwn I              Hph I                Vsp I       Hga I          Apo I
TCCAATGTAGCAGGGGCTGCTGGTGAAATTAAAGCGATGAAAGGTAAAGGTTGGATTAATCTTACAAATCCATTAGTTGCGTCACAGAAT
————————————————————————————————————————————————————————————————————————————————————————— 1620
AGGTTACATCGTCCCCGACGACCACTTTAATTTCGCTACTTTCCATTTCCAACCTAATTAGAATGTTTAGGTAATCAACGCAGTGTCTTA
 S  N  V  A  G  A  A  G  E  I  K  A  M  K  G  K  G  W  I  N  L  T  N  P  L  V  A  S  Q  N
```

FIG. 1D

```
                            Ssp I                              Msl I     SexA I              Cla I
TTTGAGTATAAATTGTCCAATATTCTTGATAAACCGTTGGAATCACTTTTTGGATACATTTCTGTGTTACCAGGTGCATTGTCTGCATAT
——————————————————————————————————————————————————————————————————————————————————————————— 1710
AAACTCATATTTAACAGGTTATAAGAACTATTTGGCAACCTTAGTGAAAAACCTATGTAAAGACACAATGGTCCACGTAACAGACGTATA
 F  E  Y  K  L  S  N  I  L  D  K  P  L  E  S  L  F  G  Y  I  S  V  L  P  G  A  L  S  A  Y

Msl I                                           Hph I
       BsrD I          BstX I                                          Mbo II
CGATACATTGCCTTGAAAAACCACGATGATGGTACAGGGCCATTGGCTTCTTATTTCAAAGGTGAAGATTTACTCTGTTCACATGACAAA
——————————————————————————————————————————————————————————————————————————————————————————— 1800
GCTATGTAACGGAACTTTTTGGTGCTACTACCATGTCCCGGTAACCGAAGAATAAAGTTTCCACTTCTAAATGAGACAAGTGTACTGTTT
 R  Y  I  A  L  K  N  H  D  D  G  T  G  P  L  A  S  Y  F  K  G  E  D  L  L  C  S  H  D  K

Asu II
                Csp45 I                       Bbs I
                Nsp V                         Bsc91 I
                Sfu I                         Mbo II     Eco57 I
GACAAAGAGAATACCAAAGCTAACTTTTTCGAAGCAAATATGTACTTGGCTGAAGACAGAATCCTTTGTTGGGAATTGGTATCAAAAAGA
——————————————————————————————————————————————————————————————————————————————————————————— 1890
CTGTTTCTCTTATGGTTTCGATTGAAAAAGCTTCGTTTATACATGAACCGACTTCTGTCTTAGGAAACAACCCTTAACCATAGTTTTTCT
 D  K  E  N  T  K  A  N  F  F  E  A  N  M  Y  L  A  E  D  R  I  L  C  W  E  L  V  S  K  R

BseN I
                        Bsr I
                        Age I
                        Bca77 I
                        BssW I
              Acs I     Cfr 10 I                                       Acs I
      Mun I   Apo I     PinA I          Hph I          Mun I           Apo I
AATGACAATTGGGTTCTTAAATTTGTTAAACTGGCAACCGGTGAAACTGATGTTCCTGAAACAATTGCAGAATTTCTTTCGCAAAGACGA
——————————————————————————————————————————————————————————————————————————————————————————— 1980
TTACTGTTAACCCAAGAATTTAAACAATTTGACCGTTGGCCACTTTGACTACAAGGACTTTGTTAACGTCTTAAAGAAAGCGTTTCTGCT
 N  D  N  W  V  L  K  F  V  K  L  A  T  G  E  T  D  V  P  E  T  I  A  E  F  L  S  Q  R  R

Vsp I
     Mbo II
     Bbv I
     Ban I                                                                            Acs I
     HgiC I                                                              Msl I        Apo I
AGATGGATTAATGGTGCCTTTTTTGCTGCTTTGTACTCCTTGTATCACTTTAGAAAAATATGGACGACTGACCATTCGTATGCTAGAAAA
——————————————————————————————————————————————————————————————————————————————————————————— 2070
TCTACCTAATTACCACGGAAAAAACGACGAAACATGAGGAACATAGTGAAATCTTTTTATACCTGCTGACTGGTAAGCATACGATCTTTT
 R  W  I  N  G  A  F  F  A  A  L  Y  S  L  Y  H  F  R  K  I  W  T  T  D  H  S  Y  A  R  K

Afl III    Acs I
        Nsp I   Apo I    Mbo II
        NspH I  EcoR I    Mun I
TTTTGGCTACATGTCGAAGAATTCATTTATCAATTGGTATCATTATTGTTTTCATTTTTTCTTTGAGTAATTTCTATTTAACATTTTAT
——————————————————————————————————————————————————————————————————————————————————————————— 2160
AAAACCGATGTACAGCTTCTTAAGTAAATAGTTAACCATAGTAATAACAAAAGTAAAAAAAGAAACTCATTAAAGATAAATTGTAAAATA
 F  W  L  H  V  E  E  F  I  Y  Q  L  V  S  L  L  F  S  F  F  S  L  S  N  F  Y  L  T  F  Y
```

```
       Acy I
       Aha II                                                              Acs I            Dsa I
       BsaH I                                                              Apo I            Nco I
       Hin1 I     Hga I          Hph I                                     Fok I            Sty I
ACGCCTCTTGATGGTGATGATTATGCAAAAGACGTTCGTACTAGAGTTGTGTTGTTTTGGATGATTGCAAATTTGGTATTTATAATGACC
────────────────────────────────────────────────────────────────────────────────────────── 2880
TGCGGAGAACTACCACTACTAATACGTTTTCTGCAAGCATGATCTCAACACAACAAAACCTACTAACGTTTAAACCATAAATATTACTGG
  T  P  L  D  G  D  D  Y  A  K  D  V  R  T  R  V  V  L  F  W  M  I  A  N  L  V  F  I  M  T

Bca77I
              BsaW I Hph I        Mbo II
ATGGTACAAGTTTACGAGCCAGGTGATACCGGAAGAAACATTTATTTGGCCTTTATTTTGTGGGCAGTGGCAGTGTTGGCTCTTGTCAGA
────────────────────────────────────────────────────────────────────────────────────────── 2970
TACCATGTTCAAATGCTCGGTCCACTATGGCCTTCTTTGTAAATAAACCGGAAATAAAACACCCGTCACCGTCACAACCGAGAACAGTCT
  M  V  Q  V  Y  E  P  G  D  T  G  R  N  I  Y  L  A  F  I  L  W  A  V  A  V  L  A  L  V  R

Eam1104 I
                                        Ear I
              Nde I                     Ksp632 I              Mbo II       Fok I     Kspl
GCTATTGGCTCTCTTGGATACTTGATACAAACATATGCACGGTTTTTTGTGGAATCGAAGAGTAAATGGATGAAACGAGGATATACCGCG
────────────────────────────────────────────────────────────────────────────────────────── 3060
CGATAACCGAGAGAACCTATGAACTATGTTTGTATACGTGCCAAAAAACACCTTAGCTTCTCATTTACCTACTTTGCTCCTATATGGCGC
  A  I  G  S  L  G  Y  L  I  Q  T  Y  A  R  F  F  V  E  S  K  S  K  W  M  K  R  G  Y  T  A Ple I
CCGAGTCACAATCCATTAAATTAG
──────────────────────── 3084         ( SEQ ID NO:1)
GGCTCAGTGTTAGGTAATTTAATC
                                      (SEQ ID NO:3)
  P  S  H  N  P  L  N                 ( SEQ ID NO:2 )
```

FIG. 1G

(SEQ ID NO: 4)

```
            10         20         30         40
   ..ııılıııı| ..ıılıııı| ..ıılıııı| ..ıılıııı|
ATAATCGTTG TGCTACTGGT AGCTAGtTTC TGCTCTCTCA  40
CTATAxGGTC tTAGTGTTGA CTGTCATGTC GATCAAGTTA  80
CTTACAGGTA AATTATTGAG TTTCAATAAG GTTGGTTTCG 120
TTGTGGCTAG TTTTTTCGAT GTTTTACAAA ATGAAAAAAA 160
ACTTAATACA TTTAAGCCAA CAGCTTATTG TAGGTGCTCC 200
           210        220        230        240
   ..ııılıııı| ..ıılıııı| ..ıılıııı| ..ıılıııı|
TTTCATTATT CGTACTTCCT ACCCCATGGA GTTTAAAATG 240
ATAAYYGAAA TTTAAAGCCA ACTAGCCAAC TAGCCAACTA 280
GCCAGCtagC MAGMCAAgAC AAAACTAATC ACAAAGACTA 320
AAAGAAAGTG TAGTTATAAA TCATTGCGAG AATTATTGCG 360
AAAxGATATT CCGCTTTTCA AAAAAACATT ATTGCGAAAA 400
           410        420        430        440
   ..ııılıııı| ..ıılıııı| ..ıılıııı| ..ıılıııı|
TCATTGCxGA xGAAAGGGGG AGTTATTTTT GGGGTACTAC 440
TATGCATGTG TTGTTGTCAA TGTCTACCAC AAAAAGGGGC 480
TTCTTTCAAT TGATAAACCT ACCAAAACAT CTGGTAATCA 520
AAAGCTACTT GTGTGAGACT ATATTTATTG TAGATTACAC 560
CCCGCTCTAC AAAGTTACCA TGAAGACAAA ACAACTTGTT 600
           610        620        630        640
   ..ııılıııı| ..ıılıııı| ..ıılıııı| ..ıılıııı|
TGAAGTTATA TGAATCGATG TTAAAaATCT GCGTCTCGTG 640
GAGAGTAACT TGATTATGTT AGGTCTGCTA TCGTTTATAC 680
TATGACCGCA TCATATACAG GACATTAGAG CATCCTAAAT 720
TAAATCATCC CATTGTTTCA AGTTTCTTTG TTTAGCAAAG 760
AGACAGTTCC AACTTGTTGT CGTCATAATT ATCGGAATAA 800
```

FIG. 3A

```
            810        820        830        840
    ....|....|  ....|....|  ....|....|  ....|....|
    TTTAAGCGAG  GAAAAGTTGT  GAAACAAATT  GAAGAGTGGA  840
    GTGTGGGGGA  GGGGGAGGGA  AACAAGGAAG  TATACCTCCA  880
    CCAAGTAGAA  CCCAAATACT  CCACGTAATC  AACAACAAGT  920
    AGCCATATAA  TTCAAAATTT  GTAGTAGTTg  GGCAAATAAT  960
    ATTTATACCC  CCCCACTCCC  CCAACCTTCC  AATTTTCCTC 1000
            1010       1020       1030       1040
    ....|....|  ....|....|  ....|....|  ....|....|
    TTCCTCTGGG  AATTTTTTTT  TTTGAAATAC  AAATCTCTTT 1040
    TAAAACCAAC  TTAAACCTAT  TAATTATGAC  AATTGAATAT 1080
    ACTTGGTGGA  AAGACGCTAC  TATTTATCAA  ATTTGGCCTG 1120
    CTTCATATAA  AGATTCCAAT  GGTGATGGAA  TTGGTGATAT 1160
    TCCAGGGATA  ATTTCTACAT  TAGATTATCT  TAAAAATTTA 1200
            1210       1220       1230       1240
    ....|....|  ....|....|  ....|....|  ....|....|
    GGAATTGATA  TTATTTGGTT  AAGTCCAATG  TATAAATCCC 1240
    CTATGGAAGA  TATGGGTTAT  GATATTAGTG  ATTATGAATC 1280
    TATAAATCCT  GATTTTGGTA  CTATGGAAGA  CATGCAAAAT 1320
    TTAATTGATG  GATGTCATGA  AAGAGGAATG  AAAATTATTT 1360
    GTGATTTAGT  AGTTAATCAT  ACATCATCTG  AACATGAATG 1400
            1410       1420       1430       1440
    ....|....|  ....|....|  ....|....|  ....|....|
    GTTTAAACAA  TCAAGATCAC  TGAAATCAAA  CCCTAAAAGA 1440
    GATTGGTATA  TTTGGAAACC  ACCGAGAATT  GACGCxAAAA 1480
    ACTGGTGxAA  AAATTACCAC  CAAATAATTG  GGGGTCATTT 1520
    TTTTCAGGAT  CAGCATGGGA  TATGATGAAT  TAACCGATGA 1560
    aTATTATTTA  AGaTTATTTG  CCAAGGGACA  ACCTGATTTA 1600
            1610       1620       1630       1640
    ....|....|  ....|....|  ....|....|  ....|....|
    AATTGGGAAA  ATGAAGAAAG  TCGTCAAGCA  ATTTATAATT 1640
    CTGCCATGAA  ATCATGGTTT  GATAAAGGTG  TTGATGGATT 1680
    TAGAATTGAT  GTTGCTGGAT  XATATTCTAA .AGATCGACCT 1720
    CxGAATCAAA  GGAA 1734
```

FIG. 3B

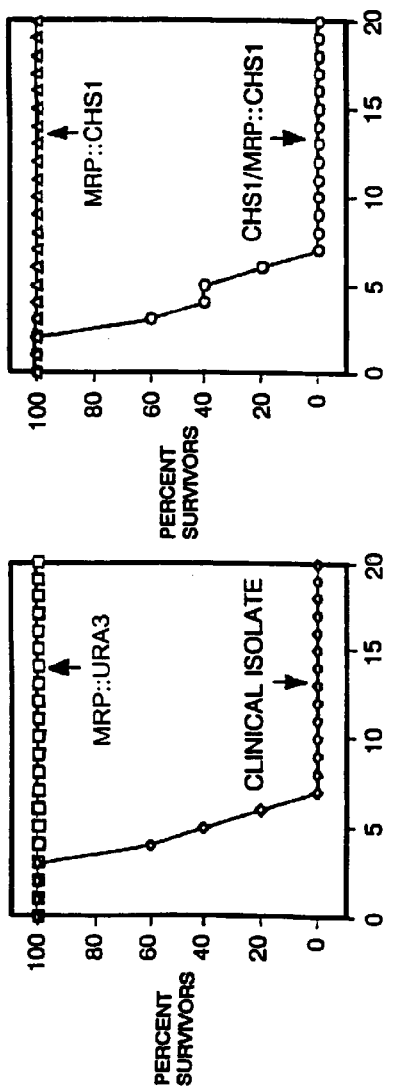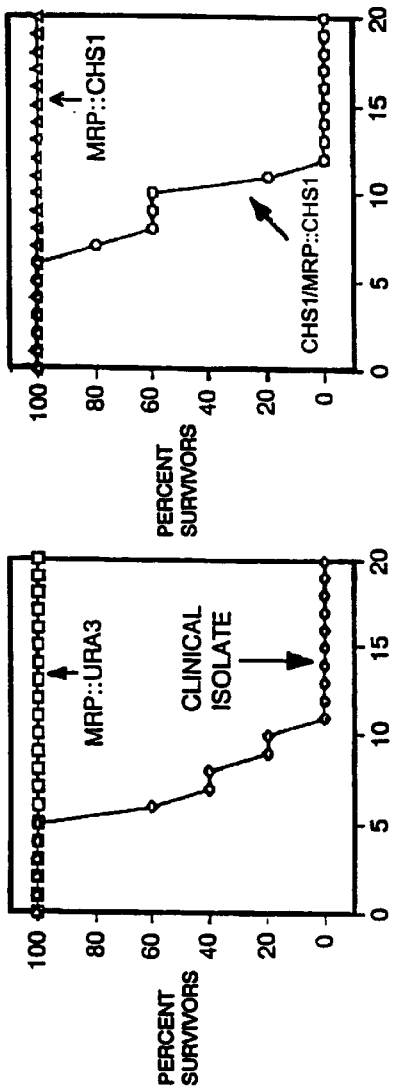
FIG. 7A
FIG. 7B
FIG. 7C
FIG. 7D

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 3084 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 1...3081

(xi) SEQUENCE DESCRIPTION: SEQ ID NO: 1:

```
ATG AAG AAT CCA TTT GAC AGT GGC AGT GAC GAT GAA GAT CCA TTT CTT      48
Met Lys Asn Pro Phe Asp Ser Gly Ser Asp Asp Glu Asp Pro Phe Leu
1               5                  10                  15

AGT AAT CCA CAA TCT GCA CCA TCA ATG CCC TAC GCA GCA TAT TTC CCA      96
Ser Asn Pro Gln Ser Ala Pro Ser Met Pro Tyr Ala Ala Tyr Phe Pro
            20                  25                  30

CTG TCG ACT AGT GGA TCT CCA TTT CAC CAA CAG CAA TCC CCA AGA CAA     144
Leu Ser Thr Ser Gly Ser Pro Phe His Gln Gln Gln Ser Pro Arg Gln
        35                  40                  45

TCA CCT AAT ATT TTT TCC AGA AGT ACT GCA AGA GCA ACT AGT GAC AGA     192
Ser Pro Asn Ile Phe Ser Arg Ser Thr Ala Arg Ala Thr Ser Asp Arg
    50                  55                  60

ACA TCG CCC CGC AAG ACA TAC CAA CCA TTG AAT TTT GAC AGT GAG GAC     240
Thr Ser Pro Arg Lys Thr Tyr Gln Pro Leu Asn Phe Asp Ser Glu Asp
65                  70                  75                  80

GAA GAT GCT AAA GAA AGC GAA TTT ATG GCT GCA ACC TCA AAG CTG AAT     288
Glu Asp Ala Lys Glu Ser Glu Phe Met Ala Ala Thr Ser Lys Leu Asn
                85                  90                  95

ATG AGC ATA TAT GAT AAT ACC CCG AAC TTA CAA TTC AAC AAA AGC GGC     336
Met Ser Ile Tyr Asp Asn Thr Pro Asn Leu Gln Phe Asn Lys Ser Gly
            100                 105                 110
```

```
GCA GCC ACA CCA AGA GCA CAA TTC ACA TCG AAA GAA TCT CCG AAA AGA      384
Ala Ala Thr Pro Arg Ala Gln Phe Thr Ser Lys Glu Ser Pro Lys Arg
        115                 120                 125

CAA AAA ACT ACT GAA GTG ACC ATT GAC TTT GAC AAT GAT GAT GAT AAC      432
Gln Lys Thr Thr Glu Val Thr Ile Asp Phe Asp Asn Asp Asp Asp Asn
130                 135                 140

AAT CAC ACC TTA GAA TTT GAA AAT GGG TCA CCT CGT CGT TCA TTT CGT      480
Asn His Thr Leu Glu Phe Glu Asn Gly Ser Pro Arg Arg Ser Phe Arg
145                 150                 155                 160

AGT AGT GCT ATA AGC AGC GAA AGA TTT TTG CCT CCT CCA CAA CCA ATT      528
Ser Ser Ala Ile Ser Ser Glu Arg Phe Leu Pro Pro Pro Gln Pro Ile
            165                 170                 175

TTC TCT CGA GAA ACA TTT GCT GAA GCC AAC TCC CGT GAA GAA GAA AAA      576
Phe Ser Arg Glu Thr Phe Ala Glu Ala Asn Ser Arg Glu Glu Glu Lys
        180                 185                 190

TCG GCA GAT CAA GAA ACA TTA GAT GAA AAA TAC GAT TAT GAT TCA TAC      624
Ser Ala Asp Gln Glu Thr Leu Asp Glu Lys Tyr Asp Tyr Asp Ser Tyr
    195                 200                 205

CAG AAG GGT TAT GAG GAA GTA GAA ACA TTG CAT TCG GAA GGT ACA GCT      672
Gln Lys Gly Tyr Glu Glu Val Glu Thr Leu His Ser Glu Gly Thr Ala
210                 215                 220

TAT AGT GGC TCA TCT TAT TTG TCG GAT GAT GCC AGT CCT GAA ACT ACA      720
Tyr Ser Gly Ser Ser Tyr Leu Ser Asp Asp Ala Ser Pro Glu Thr Thr
225                 230                 235                 240

GAT TAC TTT GGA GCT TCA ATT GAT GGT AAT ATT ATG CAC AAC ATT AAC      768
Asp Tyr Phe Gly Ala Ser Ile Asp Gly Asn Ile Met His Asn Ile Asn
            245                 250                 255

AAT GGA TAC GTA CCA AAT AGA GAA AAA ACC ATT ACC AAA AGA AAA GTG      816
Asn Gly Tyr Val Pro Asn Arg Glu Lys Thr Ile Thr Lys Arg Lys Val
        260                 265                 270

AGA TTA GTT GGT GGC AAA GCA GGT AAC TTG GTC TTG GAG AAT CCA GTT      864
Arg Leu Val Gly Gly Lys Ala Gly Asn Leu Val Leu Glu Asn Pro Val
    275                 280                 285

CCA ACA GAG TTG AGA AAA GTG TTG ACC AGA ACC GAG TCT CCA TTT GGT      912
Pro Thr Glu Leu Arg Lys Val Leu Thr Arg Thr Glu Ser Pro Phe Gly
290                 295                 300

GAG TTT ACC AAC ATG ACA TAC ACA GCG TGC ACT TCG CAG CCA GAT ACT      960
Glu Phe Thr Asn Met Thr Tyr Thr Ala Cys Thr Ser Gln Pro Asp Thr
305                 310                 315                 320

TTT TCT GCT GAA GGG TTC ACC TTA AGA GCT GCC AAA TAC GGC AGA GAA     1008
Phe Ser Ala Glu Gly Phe Thr Leu Arg Ala Ala Lys Tyr Gly Arg Glu
            325                 330                 335

ACT GAG ATT GTC ATT TGT ATA ACC ATG TAT AAT GAG GAC GAA GTT GCA     1056
Thr Glu Ile Val Ile Cys Ile Thr Met Tyr Asn Glu Asp Glu Val Ala
        340                 345                 350

TTT GCC AGA ACT ATG CAT GGT GTG ATG AAA AAT ATC GCT CAT TTG TGC     1104
Phe Ala Arg Thr Met His Gly Val Met Lys Asn Ile Ala His Leu Cys
    355                 360                 365

TCA CGC CAT AAA TCC AAA ATA TGG GGC AAA GAT AGC TGG AAA AAA GTT     1152
Ser Arg His Lys Ser Lys Ile Trp Gly Lys Asp Ser Trp Lys Lys Val
370                 375                 380

CAA GTG ATA ATT GTT GCA GAT GGT AGA AAT AAA GTT CAA CAA TCC GTT     1200
Gln Val Ile Ile Val Ala Asp Gly Arg Asn Lys Val Gln Gln Ser Val
385                 390                 395                 400

CTT GAA TTG CTT ACG GCA ACA GGC TGC TAT CAA GAA AAT TTG GCC AGG     1248
Leu Glu Leu Leu Thr Ala Thr Gly Cys Tyr Gln Glu Asn Leu Ala Arg
            405                 410                 415

CCC TAT GTC AAC AAT AGC AAA GTA AAT GCC CAT TTG TTT GAA TAT ACC     1296
Pro Tyr Val Asn Asn Ser Lys Val Asn Ala His Leu Phe Glu Tyr Thr
        420                 425                 430
```

```
ACT CAA ATA TCT ATC GAT GAG AAC TTG AAA TTC AAA GGA GAT GAA AAA         1344
Thr Gln Ile Ser Ile Asp Glu Asn Leu Lys Phe Lys Gly Asp Glu Lys
        435             440             445

AAC CTT GCA CCA GTT CAA GTC TTG TTC TGT TTG AAA GAA CTG AAC CAA         1392
Asn Leu Ala Pro Val Gln Val Leu Phe Cys Leu Lys Glu Leu Asn Gln
    450             455             460

AAG AAA ATC AAT TCC CAT AGA TGG CTT TTT AAT GCC TTT TGT CCT GTC         1440
Lys Lys Ile Asn Ser His Arg Trp Leu Phe Asn Ala Phe Cys Pro Val
465             470             475             480

TTG GAC CCC AAT GTT ATT GTT CTT TTA GAT GTG GGT ACC AAA CCC GAT         1488
Leu Asp Pro Asn Val Ile Val Leu Leu Asp Val Gly Thr Lys Pro Asp
                485             490             495

AAC CAT GCC ATT TAT AAT CTA TGG AAA GCA TTC GAT AGA GAT TCC AAT         1536
Asn His Ala Ile Tyr Asn Leu Trp Lys Ala Phe Asp Arg Asp Ser Asn
        500             505             510

GTA GCA GGG GCT GCT GGT GAA ATT AAA GCG ATG AAA GGT AAA GGT TGG         1584
Val Ala Gly Ala Ala Gly Glu Ile Lys Ala Met Lys Gly Lys Gly Trp
            515             520             525

ATT AAT CTT ACA AAT CCA TTA GTT GCG TCA CAG AAT TTT GAG TAT AAA         1632
Ile Asn Leu Thr Asn Pro Leu Val Ala Ser Gln Asn Phe Glu Tyr Lys
        530             535             540

TTG TCC AAT ATT CTT GAT AAA CCG TTG GAA TCA CTT TTT GGA TAC ATT         1680
Leu Ser Asn Ile Leu Asp Lys Pro Leu Glu Ser Leu Phe Gly Tyr Ile
545             550             555             560

TCT GTG TTA CCA GGT GCA TTG TCT GCA TAT CGA TAC ATT GCC TTG AAA         1728
Ser Val Leu Pro Gly Ala Leu Ser Ala Tyr Arg Tyr Ile Ala Leu Lys
            565             570             575

AAC CAC GAT GAT GGT ACA GGG CCA TTG GCT TCT TAT TTC AAA GGT GAA         1776
Asn His Asp Asp Gly Thr Gly Pro Leu Ala Ser Tyr Phe Lys Gly Glu
            580             585             590

GAT TTA CTC TGT TCA CAT GAC AAA GAC AAA GAG AAT ACC AAA GCT AAC         1824
Asp Leu Leu Cys Ser His Asp Lys Asp Lys Glu Asn Thr Lys Ala Asn
        595             600             605

TTT TTC GAA GCA AAT ATG TAC TTG GCT GAA GAC AGA ATC CTT TGT TGG         1872
Phe Phe Glu Ala Asn Met Tyr Leu Ala Glu Asp Arg Ile Leu Cys Trp
    610             615             620

GAA TTG GTA TCA AAA AGA AAT GAC AAT TGG GTT CTT AAA TTT GTT AAA         1920
Glu Leu Val Ser Lys Arg Asn Asp Asn Trp Val Leu Lys Phe Val Lys
625             630             635             640

CTG GCA ACC GGT GAA ACT GAT GTT CCT GAA ACA ATT GCA GAA TTT CTT         1968
Leu Ala Thr Gly Glu Thr Asp Val Pro Glu Thr Ile Ala Glu Phe Leu
            645             650             655

TCG CAA AGA CGA AGA TGG ATT AAT GGT GCC TTT TTT GCT GCT TTG TAC         2016
Ser Gln Arg Arg Arg Trp Ile Asn Gly Ala Phe Phe Ala Ala Leu Tyr
            660             665             670

TCC TTG TAT CAC TTT AGA AAA ATA TGG ACG ACT GAC CAT TCG TAT GCT         2064
Ser Leu Tyr His Phe Arg Lys Ile Trp Thr Thr Asp His Ser Tyr Ala
        675             680             685

AGA AAA TTT TGG CTA CAT GTC GAA GAA TTC ATT TAT CAA TTG GTA TCA         2112
Arg Lys Phe Trp Leu His Val Glu Glu Phe Ile Tyr Gln Leu Val Ser
    690             695             700

TTA TTG TTT TCA TTT TTT TCT TTG AGT AAT TTC TAT TTA ACA TTT TAT         2160
Leu Leu Phe Ser Phe Phe Ser Leu Ser Asn Phe Tyr Leu Thr Phe Tyr
705             710             715             720

TTT TTG ACA GGT TCA TTG GTG TCT TAC AAA AGT CTT GGT AAA AAA GGT         2208
Phe Leu Thr Gly Ser Leu Val Ser Tyr Lys Ser Leu Gly Lys Lys Gly
            725             730             735

GGA TTT TGG ATT TTC ACA TTA TTC AAT TAT CTC TGT ATC GGT GTT TTG         2256
Gly Phe Trp Ile Phe Thr Leu Phe Asn Tyr Leu Cys Ile Gly Val Leu
```

```
                    740                 745                 750
ACA TCT TTG TTC ATT GTC TCC ATT GGT AAT AGA CCA CAT GCA TCA AAG        2304
Thr Ser Leu Phe Ile Val Ser Ile Gly Asn Arg Pro His Ala Ser Lys
        755                 760                 765

AAT ATT TTC AAA ACA TTA ATC ATA TTG TTA ACC ATA TGT GCA TTA TAC        2352
Asn Ile Phe Lys Thr Leu Ile Ile Leu Leu Thr Ile Cys Ala Leu Tyr
        770                 775                 780

GCA TTG GTG GTT GGA TTT GTG TTT GTT ATC AAT ACT ATT GCT ACT TTT        2400
Ala Leu Val Val Gly Phe Val Phe Val Ile Asn Thr Ile Ala Thr Phe
785                 790                 795                 800

GGA ACC GGT GGA ACA TCT ACC TAT GTG CTC GTT AGT ATT GTG GTT TCA        2448
Gly Thr Gly Gly Thr Ser Thr Tyr Val Leu Val Ser Ile Val Val Ser
                    805                 810                 815

TTG TTG TCC ACC TAT GGT CTT TAT ACG TTA ATG TCC ATT TTG TAC TTG        2496
Leu Leu Ser Thr Tyr Gly Leu Tyr Thr Leu Met Ser Ile Leu Tyr Leu
                820                 825                 830

GAC CCA TGG CAC ATG TTG ACT TGT TCT GTA CAA TAC TTT TTG ATG ATT        2544
Asp Pro Trp His Met Leu Thr Cys Ser Val Gln Tyr Phe Leu Met Ile
            835                 840                 845

CCA TCG TAC ACT TGT ACA TTA CAA ATA TTT GCA TTT TGT AAT ACT CAC        2592
Pro Ser Tyr Thr Cys Thr Leu Gln Ile Phe Ala Phe Cys Asn Thr His
        850                 855                 860

GAT GTC TCG TGG GGT ACA AAA GGT GAC AAC AAT CCA AAA GAA GAT TTG        2640
Asp Val Ser Trp Gly Thr Lys Gly Asp Asn Asn Pro Lys Glu Asp Leu
865                 870                 875                 880

AGT AAT CAG TAC ATT ATT GAG AAA AAT GCC AGT GGA GAA TTT GAG GCT        2688
Ser Asn Gln Tyr Ile Ile Glu Lys Asn Ala Ser Gly Glu Phe Glu Ala
                    885                 890                 895

GTT ATT GTT GAT ACA AAT ATC GAT GAA GAT TAC CTT GAG ACA TTA TAT        2736
Val Ile Val Asp Thr Asn Ile Asp Glu Asp Tyr Leu Glu Thr Leu Tyr
                900                 905                 910

AAT ATC AGG TCA AAG AGA TCA AAC AAA AAA GTG GCT TTG GGC CAT TCT        2784
Asn Ile Arg Ser Lys Arg Ser Asn Lys Lys Val Ala Leu Gly His Ser
            915                 920                 925

GAA AAG ACG CCT CTT GAT GGT GAT GAT TAT GCA AAA GAC GTT CGT ACT        2832
Glu Lys Thr Pro Leu Asp Gly Asp Asp Tyr Ala Lys Asp Val Arg Thr
        930                 935                 940

AGA GTT GTG TTG TTT TGG ATG ATT GCA AAT TTG GTA TTT ATA ATG ACC        2880
Arg Val Val Leu Phe Trp Met Ile Ala Asn Leu Val Phe Ile Met Thr
945                 950                 955                 960

ATG GTA CAA GTT TAC GAG CCA GGT GAT ACC GGA AGA AAC ATT TAT TTG        2928
Met Val Gln Val Tyr Glu Pro Gly Asp Thr Gly Arg Asn Ile Tyr Leu
                    965                 970                 975

GCC TTT ATT TTG TGG GCA GTG GCA GTG TTG GCT CTT GTC AGA GCT ATT        2976
Ala Phe Ile Leu Trp Ala Val Ala Val Leu Ala Leu Val Arg Ala Ile
                980                 985                 990

GGC TCT CTT GGA TAC TTG ATA CAA ACA TAT GCA CGG TTT TTT GTG GAA        3024
Gly Ser Leu Gly Tyr Leu Ile Gln Thr Tyr Ala Arg Phe Phe Val Glu
            995                 1000                1005

TCG AAG AGT AAA TGG ATG AAA CGA GGA TAT ACC GCG CCG AGT CAC AAT        3072
Ser Lys Ser Lys Trp Met Lys Arg Gly Tyr Thr Ala Pro Ser His Asn
        1010                1015                1020

CCA TTA AAT TAG                                                         3084
Pro Leu Asn
1025
```

(2) INFORMATION FOR SEQ ID NO: 2:

(i) SEQUENCE CHARACTERISTICS:
        (A) LENGTH: 1027 amino acids (B) TYPE: amino acid
(D) TOPOLOGY: linear (ii) MOLECULE TYPE: protein (v) FRAGMENT TYPE: internal (xi) SEQUENCE DESCRIPTION: SEQ ID NO: 2:

```
Met Lys Asn Pro Phe Asp Ser Gly Ser Asp Asp Glu Asp Pro Phe Leu
 1               5                  10                  15

Ser Asn Pro Gln Ser Ala Pro Ser Met Pro Tyr Ala Ala Tyr Phe Pro
                20                  25                  30

Leu Ser Thr Ser Gly Ser Pro Phe His Gln Gln Ser Pro Arg Gln
                35                  40                  45

Ser Pro Asn Ile Phe Ser Arg Ser Thr Ala Arg Ala Thr Ser Asp Arg
        50                  55                  60

Thr Ser Pro Arg Lys Thr Tyr Gln Pro Leu Asn Phe Asp Ser Glu Asp
 65                  70                  75                  80

Glu Asp Ala Lys Glu Ser Glu Phe Met Ala Ala Thr Ser Lys Leu Asn
                85                  90                  95

Met Ser Ile Tyr Asp Asn Thr Pro Asn Leu Gln Phe Asn Lys Ser Gly
               100                 105                 110

Ala Ala Thr Pro Arg Ala Gln Phe Thr Ser Lys Glu Ser Pro Lys Arg
               115                 120                 125

Gln Lys Thr Thr Glu Val Thr Ile Asp Phe Asp Asn Asp Asp Asn
130                 135                 140

Asn His Thr Leu Glu Phe Glu Asn Gly Ser Pro Arg Arg Ser Phe Arg
145                 150                 155                 160

Ser Ser Ala Ile Ser Ser Glu Arg Phe Leu Pro Pro Gln Pro Ile
               165                 170                 175

Phe Ser Arg Glu Thr Phe Ala Glu Ala Asn Ser Arg Glu Glu Glu Lys
               180                 185                 190

Ser Ala Asp Gln Glu Thr Leu Asp Glu Lys Tyr Asp Tyr Asp Ser Tyr
               195                 200                 205

Gln Lys Gly Tyr Glu Glu Val Glu Thr Leu His Ser Glu Gly Thr Ala
        210                 215                 220

Tyr Ser Gly Ser Ser Tyr Leu Ser Asp Asp Ala Ser Pro Glu Thr Thr
225                 230                 235                 240

Asp Tyr Phe Gly Ala Ser Ile Asp Gly Asn Ile Met His Asn Ile Asn
               245                 250                 255

Asn Gly Tyr Val Pro Asn Arg Glu Lys Thr Ile Thr Lys Arg Lys Val
               260                 265                 270

Arg Leu Val Gly Gly Lys Ala Gly Asn Leu Val Leu Glu Asn Pro Val
       275                 280                 285

Pro Thr Glu Leu Arg Lys Val Leu Thr Arg Thr Glu Ser Pro Phe Gly
       290                 295                 300

Glu Phe Thr Asn Met Thr Tyr Thr Ala Cys Thr Ser Gln Pro Asp Thr
305                 310                 315                 320

Phe Ser Ala Glu Gly Phe Thr Leu Arg Ala Ala Lys Tyr Gly Arg Glu
               325                 330                 335

Thr Glu Ile Val Ile Cys Ile Thr Met Tyr Asn Glu Asp Glu Val Ala
               340                 345                 350

Phe Ala Arg Thr Met His Gly Val Met Lys Asn Ile Ala His Leu Cys
       355                 360                 365

Ser Arg His Lys Ser Lys Ile Trp Gly Lys Asp Ser Trp Lys Lys Val
```

-continued

```
            370                 375                 380
Gln Val Ile Ile Val Ala Asp Gly Arg Asn Lys Val Gln Gln Ser Val
385                 390                 395                 400

Leu Glu Leu Leu Thr Ala Thr Gly Cys Tyr Gln Glu Asn Leu Ala Arg
                405                 410                 415

Pro Tyr Val Asn Asn Ser Lys Val Asn Ala His Leu Phe Glu Tyr Thr
                420                 425                 430

Thr Gln Ile Ser Ile Asp Glu Asn Leu Lys Phe Lys Gly Asp Glu Lys
                435                 440                 445

Asn Leu Ala Pro Val Gln Val Leu Phe Cys Leu Lys Glu Leu Asn Gln
            450                 455                 460

Lys Lys Ile Asn Ser His Arg Trp Leu Phe Asn Ala Phe Cys Pro Val
465                 470                 475                 480

Leu Asp Pro Asn Val Ile Val Leu Leu Asp Val Gly Thr Lys Pro Asp
                485                 490                 495

Asn His Ala Ile Tyr Asn Leu Trp Lys Ala Phe Asp Arg Asp Ser Asn
                500                 505                 510

Val Ala Gly Ala Ala Gly Glu Ile Lys Ala Met Lys Gly Lys Gly Trp
            515                 520                 525

Ile Asn Leu Thr Asn Pro Leu Val Ala Ser Gln Asn Phe Glu Tyr Lys
            530                 535                 540

Leu Ser Asn Ile Leu Asp Lys Pro Leu Glu Ser Leu Phe Gly Tyr Ile
545                 550                 555                 560

Ser Val Leu Pro Gly Ala Leu Ser Ala Tyr Arg Tyr Ile Ala Leu Lys
                565                 570                 575

Asn His Asp Asp Gly Thr Gly Pro Leu Ala Ser Tyr Phe Lys Gly Glu
                580                 585                 590

Asp Leu Leu Cys Ser His Asp Lys Asp Lys Glu Asn Thr Lys Ala Asn
            595                 600                 605

Phe Phe Glu Ala Asn Met Tyr Leu Ala Glu Asp Arg Ile Leu Cys Trp
610                 615                 620

Glu Leu Val Ser Lys Arg Asn Asp Asn Trp Val Leu Lys Phe Val Lys
625                 630                 635                 640

Leu Ala Thr Gly Glu Thr Asp Val Pro Glu Thr Ile Ala Glu Phe Leu
                645                 650                 655

Ser Gln Arg Arg Arg Trp Ile Asn Gly Ala Phe Phe Ala Ala Leu Tyr
                660                 665                 670

Ser Leu Tyr His Phe Arg Lys Ile Trp Thr Thr Asp His Ser Tyr Ala
            675                 680                 685

Arg Lys Phe Trp Leu His Val Glu Glu Phe Ile Tyr Gln Leu Val Ser
            690                 695                 700

Leu Leu Phe Ser Phe Phe Ser Leu Ser Asn Phe Tyr Leu Thr Phe Tyr
705                 710                 715                 720

Phe Leu Thr Gly Ser Leu Val Ser Tyr Lys Ser Leu Gly Lys Lys Gly
                725                 730                 735

Gly Phe Trp Ile Phe Thr Leu Phe Asn Tyr Leu Cys Ile Gly Val Leu
                740                 745                 750

Thr Ser Leu Phe Ile Val Ser Ile Gly Asn Arg Pro His Ala Ser Lys
            755                 760                 765

Asn Ile Phe Lys Thr Leu Ile Ile Leu Thr Ile Cys Ala Leu Tyr
            770                 775                 780

Ala Leu Val Val Gly Phe Val Phe Val Ile Asn Thr Ile Ala Thr Phe
785                 790                 795                 800
```

```
Gly Thr Gly Gly Thr Ser Thr Tyr Val Leu Val Ser Ile Val Val Ser
                805                 810                 815
Leu Leu Ser Thr Tyr Gly Leu Tyr Thr Leu Met Ser Ile Leu Tyr Leu
            820                 825                 830
Asp Pro Trp His Met Leu Thr Cys Ser Val Gln Tyr Phe Leu Met Ile
        835                 840                 845
Pro Ser Tyr Thr Cys Thr Leu Gln Ile Phe Ala Phe Cys Asn Thr His
    850                 855                 860
Asp Val Ser Trp Gly Thr Lys Gly Asp Asn Pro Lys Glu Asp Leu
865                 870                 875                 880
Ser Asn Gln Tyr Ile Ile Glu Lys Asn Ala Ser Gly Glu Phe Glu Ala
            885                 890                 895
Val Ile Val Asp Thr Asn Ile Asp Glu Asp Tyr Leu Glu Thr Leu Tyr
        900                 905                 910
Asn Ile Arg Ser Lys Arg Ser Asn Lys Lys Val Ala Leu Gly His Ser
    915                 920                 925
Glu Lys Thr Pro Leu Asp Gly Asp Asp Tyr Ala Lys Asp Val Arg Thr
930                 935                 940
Arg Val Val Leu Phe Trp Met Ile Ala Asn Leu Val Phe Ile Met Thr
945                 950                 955                 960
Met Val Gln Val Tyr Glu Pro Gly Asp Thr Gly Arg Asn Ile Tyr Leu
                965                 970                 975
Ala Phe Ile Leu Trp Ala Val Ala Val Leu Ala Leu Val Arg Ala Ile
            980                 985                 990
Gly Ser Leu Gly Tyr Leu Ile Gln Thr Tyr Ala Arg Phe Phe Val Glu
        995                1000                1005
Ser Lys Ser Lys Trp Met Lys Arg Gly Tyr Thr Ala Pro Ser His Asn
    1010                1015                1020
Pro Leu Asn
1025

(2) INFORMATION FOR SEQ ID NO: 3:

(i) SEQUENCE CHARACTERISTICS:
        (A) LENGTH: 3084 base pairs
        (B) TYPE: nucleic acid
        (C) STRANDEDNESS: double
        (D) TOPOLOGY: linear (xi) SEQUENCE DESCRIPTION: SEQ ID NO: 3:

TACTTCTTAG GTAAACTGTC ACCGTCACTG CTACTTCTAG GTAAAGAATC ATTAGGTGTT        60

AGACGTGGTA GTTACGGGAT GCGTCGTATA TGATCACTGT CTTGTAGCGG GGCGTTCTGT       120

ATGGTTGGTA ACTTAAAACT GYCACTCCTG CTTCTACGAT TTCTTTCGCT TAAATACCGA       180

AAGGGTGACA GCTGATCACC TAGAGGTAAA GTGGTTGTCG TTAGGGGTTC TGTTAGTGGA       240

TTATAAAAAA GGTCTTCATG ACGTTCTCGT CGTTGGAGTT TCGACTTATA CTCGTATATA       300

CTATTATGGG GCTTGAATGT TAAGTTGTTT TCGCCGCGTC GGTGTGGTTC TCGTGTTAAG       360

TGTAGCTTTC TTAGAGGCTT TTCTGTTTTT TGATGACTTC ACTGGTAACT GAAACTGTTA       420

CTACTACTAT TGTTAGTGTG GAATCTTAAA CTTTTACCCA GTGGAGCAGC AAGTAAAGCA       480

TCATCACGAT ATTCGTCGCT TTCTAAAAAC GGAGGAGGTG TTGGTTAAAA GAGAGCTCTT       540

TGTAAACGAC TTCGGTTGAG GGCACTTCTT CTTTTTAGCC GTCTAGTTCT TTGTAATCTA       600

CTTTTTATGC TAATACTAAG TATGGTCTTC CCAATACTCC TTCATCTTTG TAACGTAAGC       660
```

-continued

```
CTTCCATGTC GAATATCACC GAGTAGAATA AACAGCCTAC TACGGTCAGG ACTTTGATGT     720

CTAATGAAAC CTCGAAGTTA ACTACCATTA TAATACGTGT TGTAATTGTT ACCTATGCAT     780

GGTTTATCTC TTTTTTGGTA ATGGTTTTCT TTTCACTCTA ATCAACCACC GTTTCGTCCA     840

TTGAACCAGA ACCTCTTAGG TCAAGGTTGT CTCAACTCTT TTCACAACTG GTCTTGGCTC     900

AGAGGTAAAC CACTCAAATG GTTGTACTGT ATGTGTCGCA CGTGAAGCGT CGGTCTATGA     960

AAAAGACGAC TTCCCAAGTG GAATTCTCGA CGGTTTATGC CGTCTCTTTG ACTCTAACAG    1020

TAAACATATT GGTACATATT ACTCCTGCTT CAACGTAAAC GGTCTTGATA CGTACCACAC    1080

TACTTTTTAT AGCGAGTAAA CACGAGTGCG GTATTTAGGT TTTATACCCC GTTTCTATCG    1140

ACCTTTTTTC AAGTTCACTA TTAACAACGT CTACCATCTT TATTTCAAGT TGTTAGGCAA    1200

GAACTTAACG AATGCCGTTG TCCGACGATA GTTCTTTTAA ACCGGTCCGG GATACAGTTG    1260

TTATCGTTTC ATTACGGGT AAACAAACTT ATATGGTGAG TTTATAGATA GCTACTCTTG    1320

AACTTTAAGT TTCCTCTACT TTTTTTGGAA CGTGGTCAAG TTCAGAACAA GACAAACTTT    1380

CTTGACTTGG TTTTCTTTTA GTTAAGGGTA TCTACCGAAA AATTACGGAA AACAGGACAG    1440

AACCTGGGGT TACAATAACA AGAAAATCTA CACCCATGGT TTGGGCTATT GGTACGGTAA    1500

ATATTAGATA CCTTTCGTAA GCTATCTCTA AGGTTACATC GTCCCCGACG ACCACTTTAA    1560

TTTCGCTACT TTCCATTTCC AACCTAATTA GAATGTTTAG GTAATCAACG CAGTGTCTTA    1620

AAACTCATAT TTAACAGGTT ATAAGAACTA TTTGGCAACC TTAGTGAAAA ACCTATGTAA    1680

AGACACAATG GTCCACGTAA CAGACGTATA GCTATGTAAC GGAACTTTTT GGTGCTACTA    1740

CCATGTCCCG GTAACCGAAG AATAAAGTTT CCACTTCTAA ATGAGACAAG TGTACTGTTT    1800

CTGTTTCTCT TATGGTTTCG ATTGAAAAAG CTTCGTTTAT ACATGAACCG ACTTCTGTCT    1860

TAGGAAACAA CCCTTAACCA TAGTTTTTCT TTACTGTTAA CCCAAGAATT TAAACAATTT    1920

GACCGTTGGC CACTTTGACT ACAAGGACTT TGTTAACGTC TTAAAGAAAG CGTTTCTGCT    1980

TCTACCTAAT TACCACGGAA AAAACGACGA AACATGAGGA ACATAGTGAA ATCTTTTTAT    2040

ACCTGCTGAC TGGTAAGCAT ACGATCTTTT AAAACCGATG TACAGCTTCT TAAGTAAATA    2100

GTTAACCATA GTAATAACAA AAGTAAAAAA AGAAACTCAT TAAAGATAAA TTGTAAAATA    2160

AAAAACTGTC CAAGTAACCA CAGAATGTTT TCAGAACCAT TTTTTCCACC TAAAACCTAA    2220

AAGTGTAATA AGTTAATAGA GACATAGCCA CAAAACTGTA GAAACAAGTA ACAGAGGTAA    2280

CCATTATCTG GTGTACGTAG TTTCTTATAA AAGTTTTGTA ATTAGTATAA CAATTGGTAT    2340

ACACGTAATA TGCGTAACCA CCAACCTAAA CACAAACAAT AGTTATGATA ACGATGAAAA    2400

CCTTGGCCAC CTTGTAGATG GATACACGAG CAATCATAAC ACCAAAGTAA CAACAGGTGG    2460

ATACCAGAAA TATGCAATTA CAGGTAAAAC ATGAACCTGG GTACCGTGTA CAACTGAACA    2520

AGACATGTTA TGAAAAACTA CTAAGGTAGC ATGTGAACAT GTAATGTTTA TAAACGTAAA    2580

ACATTATGAG TGCTACAGAG CACCCCATGT TTTCCACTGT TGTTAGGTTT TCTTCTAAAC    2640

TCATTAGTCA TGTAATAACT CTTTTTACGG TCACCTCTTA AACTCCGACA ATAACAACTA    2700

TGTTTATAGC TACTTCTAAT GGAACTCTGT AATATATTAT AGTCCAGTTT CTCTAGTTTG    2760

TTTTTTCACC GAAACCCGGT AAGACTTTTC TGCGGAGAAC TACCACTACT AATACGTTTT    2820

CTGCAAGCAT GATCTCAACA CAACAAAACC TACTAACGTT TAAACCATAA ATATTACTGG    2880

TACCATGTTC AAATGCTCGG TCCACTATGG CCTTCTTTGT AAATAAACCG GAAATAAAAC    2940

ACCCGTCACC GTCACAACCG AGAACAGTCT CGATAACCGA GAGAACCTAT GAACTATGTT    3000

TGTATACGTG CCAAAAAACA CCTTAGCTTC TCATTTACCT ACTTTGCTCC TATATGGCGC    3060
```

```
GGCTCAGTGT TAGGTAATTT AATC                                              3084

(2) INFORMATION FOR SEQ ID NO: 4:

(i) SEQUENCE CHARACTERISTICS:
          (A) LENGTH: 1734 base pairs
          (B) TYPE: nucleic acid
          (C) STRANDEDNESS: single
          (D) TOPOLOGY: linear (xi) SEQUENCE DESCRIPTION: SEQ ID NO: 4:

ATAATCGTTG TGCTACTGGT AGCTAGTTTC TGCTCTCTCA CTATANGGTC TTAGTGTTGA          60

CTGTCATGTC GATCAAGTTA CTTACAGGTA AATTATTGAG TTTCAATAAG GTTGGTTTCG         120

TTGTGGCTAG TTTTTTCGAT GTTTTACAAA ATGAAAAAAA ACTTAATACA TTTAAGCCAA         180

CAGCTTATTG TAGGTGCTCC TTTCATTATT CGTACTTCCT ACCCCATGGA GTTTAAAATG         240

ATAAYYGAAA TTTAAAGCCA ACTAGCCAAC TAGCCAACTA GCCAGCTAGC MAGMCAAGAC         300

AAAACTAATC ACAAAGACTA AAAGAAAGTG TAGTTATAAA TCATTGCGAG AATTATTGCG         360

AAANGATATT CCGCTTTTCA AAAAAACATT ATTGCGAAAA TCATTGCNGA NGAAAGGGGG         420

AGTTATTTTT GGGGTACTAC TATGCATGTG TTGTTGTCAA TGTCTACCAC AAAAAGGGGC         480

TTCTTTCAAT TGATAAACCT ACCAAAACAT CTGGTAATCA AAAGCTACTT GTGTGAGACT         540

ATATTTATTG TAGATTACAC CCCGCTCTAC AAAGTTACCA TGAAGACAAA ACAACTTGTT         600

TGAAGTTATA TGAATCGATG TTAAAAATCT GCGTCTCGTG GAGAGTAACT TGATTATGTT         660

AGGTCTGCTA TCGTTTATAC TATGACCGCA TCATATACAG GACATTAGAG CATCCTAAAT         720

TAAATCATCC CATTGTTTCA AGTTTCTTTG TTTAGCAAAG AGACAGTTCC AACTTGTTGT         780

CGTCATAATT ATCGGAATAA TTTAAGCGAG GAAAAGTTGT GAAACAAATT GAAGAGTGGA         840

GTGTGGGGGA GGGGGAGGGA AACAAGGAAG TATACCTCCA CCAAGTAGAA CCCAAATACT         900

CCACGTAATC AACAACAAGT AGCCATATAA TTCAAAATTT GTAGTAGTTG GGCAAATAAT         960

ATTTATACCC CCCCACTCCC CCAACCTTCC AATTTTCCTC TTCCTCTGGG AATTTTTTTT        1020

TTTGAAATAC AAATCTCTTT TAAAACCAAC TTAAACCTAT TAATTATGAC AATTGAATAT        1080

ACTTGGTGGA AAGACGCTAC TATTTATCAA ATTTGGCCTG CTTCATATAA AGATTCCAAT        1140

GGTGATGGAA TTGGTGATAT TCCAGGGATA ATTTCTACAT TAGATTATCT TAAAAATTTA        1200

GGAATTGATA TTATTTGGTT AAGTCCAATG TATAAATCCC CTATGGAAGA TATGGGTTAT        1260

GATATTAGTG ATTATGAATC TATAAATCCT GATTTTGGTA CTATGGAAGA CATGCAAAAT        1320

TTAATTGATG GATGTCATGA AAGAGGAATG AAAATTATTT GTGATTTAGT AGTTAATCAT        1380

ACATCATCTG AACATGAATG GTTAAACAA TCAAGATCAC TGAAATCAAA CCCTAAAAGA         1440

GATTGGTATA TTTGGAAACC ACCGAGAATT GACGCNAAAA ACTGGTGNAA AAATTACCAC        1500

CAAATAATTG GGGGTCATTT TTTTCAGGAT CAGCATGGGA TATGATGAAT TAACCGATGA        1560

ATATTATTTA AGATTATTTG CCAAGGGACA ACCTGATTTA AATTGGGAAA ATGAAGAAAG        1620

TCGTCAAGCA ATTTATAATT CTGCCATGAA ATCATGGTTT GATAAAGGTG TTGATGGATT        1680

TAGAATTGAT GTTGCTGGAT NATATTCTAA AGATCGACCT CNGAATCAAA GGAA             1734

(2) INFORMATION FOR SEQ ID NO: 5:

(i) SEQUENCE CHARACTERISTICS:
          (A) LENGTH: 26 base pairs
          (B) TYPE: nucleic acid
          (C) STRANDEDNESS: single
```

```
            (D) TOPOLOGY: linear (xi) SEQUENCE DESCRIPTION: SEQ ID NO: 5:

GGAGGAGTCG ACATGACAGT CAACAC                                            26

(2) INFORMATION FOR SEQ ID NO: 6:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 6:

CGCATTAAAG CTCTAGAAGA ACCACC                                            26
```

IDENTIFICATION OF EUKARYOTIC GROWTH-RELATED GENES AND PROMOTER ISOLATION VECTOR AND METHOD OF USE

RELATED APPLICATION INFORMATION

This application is a divisional of application Ser. No. 09/004,225, filed Jan. 8, 1998 now U.S. Pat No. 6,020,133, which is a divisional of application Ser. No. 08/551,437, filed Nov. 1, 1995 now U.S. Pat. No. 5,824,545.

FIELD OF THE INVENTION

This invention relates generally to the field of gene expression and specifically to genes essential for growth and to a vector and a method for the identification of such genes, as well as identification of eukaryotic promoters.

BACKGROUND OF THE INVENTION

Many eukaryotic genes are regulated in an inducible, cell type-specific or constitutive manner. There are several types of structural elements which are involved in the regulation of gene expression. There are cis-acting elements, located in the proximity of, or within, genes which serve to bind sequence-specific DNA binding proteins, as well as trans-acting factors. The binding of proteins to DNA is responsible for the initiation, maintenance, or down-regulation of transcription of genes.

The cis-acting elements which control genes are called promoters, enhancers or silencers. Promoters are positioned next to the start site of transcription and function in an orientation-dependent manner, while enhancer and silencer elements, which modulate the activity of promoters, are flexible with respect to their orientation and distance from the start site of transcription.

For many years, various drugs have been tested for their ability to alter the expression of genes or the translation of their messages into protein products. One problem with existing drug therapy is that it tends to act indiscriminately on genes and promoters and therefore affects healthy cells as well as neoplastic cells. Likewise, in the case of a pathogen-associated disease, it is critical to administer a pathogen-specific therapy to avoid any detrimental effect on the non-infected cells.

Chitin, a linear β-1,4 linked polymer of N-acetylglucosamine, is present in the cell walls of all true fungi, but is absent from mammalian cells. Studies in *S. cerevisiae* (reviewed in Bulawa, C., *Mol. Cell. Biol.* 12:1764, 1992; Cabib et al., *Arch. Med. Res.,* 24:301, 1993) have shown that the synthesis of chitin is surprisingly complex, requiring at least three isozymes encoded by the CHS1, CHS2, and CSD2 genes. In cell-free extracts, all of the isozymes catalyze the formation of chitin using UDP-N-acetylglucosamine as the substrate. In cells, each isozyme makes chitin at a unique location in the cell during a specified interval of the cell cycle. Genetic analyses indicate that CHS2 is involved in the synthesis of the chitin-rich primary septum that separates mother and daughter cells, CSD2 is required for synthesis of the chitin rings, and CHS1 plays a role in cell wall repair. Thus, the three isozymes are not functionally redundant and do not substitute for one another.

Chitin synthase genes have been identified from a diverse group of fungi, and analysis of the deduced amino acid sequences of these genes has lead to the identification of two chitin synthase gene families (Bowen, et al., *Proc. Natl. Acad. Sci., USA,* 89:519, 1992). Members of one family are related to the *S. cerevisiae* CHS genes (CHS family). Based on sequence analyses, the CHS family can be subdivided into classes I, II, and III. Members of the second family are related to the *S. cerevisiae* CSD2 gene.

The functions of class II CHS genes have been investigated in a number of fungi by gene disruption. In *S. cerevisiae,* the class II CHS mutant (designated chs2) is defective in cell separation (Bulawa and Osmond, *Proc. Natl. Acad. Sci., USA,* 87:7424, 1990; Shaw et al., *J. Cell Biol.,* 114(1):111, 1990). In *A. nidulans* (Yanai et al., *Biosci.* 58(10):1828, 1994) and *U. maydis* (Gold and Kronstad, *Molecular Microbiology,* 11(5):897, 1994), class II CHS mutants (designated chsA and chs1, respectively) have no obvious phenotype. Thus, all of the class II CHS genes studied to date are nonessential for growth. In addition, Young, et al. identified chitin synthase gene which encodes only part of the chitin synthase activity in *C. albicans* (*Molec. Micro.,* 4(2):197, 1990).

There have been methods designed to identify virulence genes of microorganisms involved in pathogenesis. For example, Osbourn, et al. utilized a promoter-probe plasmid for use in identifying promoters that are induced in vivo in plants by *Xanthomonas campestris* (*EMBO, J.* 6:23, 1987). Random chromosomal DNA fragments were cloned into a site in front of a promoterless chloramphenicol acetyltransferase gene contained in the plasmid and the plasmids were transferred into Xanthomonas to form a library. Individual transconjugates were introduced into chloramphenicol-treated seedlings to determine whether the transconjugate displayed resistance to chloramphenicol in the plant.

Knapp, et al., disclosed a method for identifying virulence genes based on their coordinate expression with other known virulence genes under defined laboratory conditions (*J. Bacteriol.,* 170:5059, 1988). Mahan, et al., (U.S. Pat. No. 5,434,065) described an in vivo genetic system to select for microbial genes that are specifically induced when microbes infect their host. The method depends on complementing the growth of an auxotrophic or antibiotic sensitive microorganism by integrating an expression vector by way of homologous recombination into the auxotrophic or antibiotic sensitive microorganism's chromosome and inducing the expression of a synthetic operon which encodes transcripts, the expression of which are easily monitored in vitro following in vivo complementation.

These systems all describe methods of identifying genes involved in pathogenesis in bacterial-host systems. There is a need to identify specific targets of eukaryotic pathogens, e.g., fungi, in an infected cell which are associated with the expression of genes whose expression products are implicated in disease, in order to increase efficacy of treatment of infected cells and to increase the efficiency of developing drugs effective against genes essential for survival of these pathogens.

The present invention provides a method for identifying targets essential for growth as well as specific targets identified by the method.

SUMMARY OF THE INVENTION

The present invention provides a yeast chitin synthase (CHS1) polypeptide and a polynucleotide encoding the polypeptide. In the present invention, the class II CHS gene of *C. albicans* (encoded by the CHS1 gene) is shown to be essential for growth under laboratory conditions and for colonization of tissues during infection in vivo. Thus, CHS1 is a target for the development of antifungal drugs.

CHS1 inhibitors are useful for inhibiting the growth of a yeast. Such CHS1 inhibitory reagents include, e.g., anti-CHS1 antibodies and CHS1 antisense molecules.

CHS1 can be used to determine whether a compound affects (e.g., inhibits) CHS1 activity, by incubating the compound with CHS1 polypeptide, or with a recombinant cell expressing CHS1, under conditions sufficient to allow the components to interact, and then determining the effect of the compound on CHS1 activity or expression.

The invention also provides a vector for identifying a eukaryotic regulatory polynucleotide, including a selectable marker gene; a restriction endonuclease site located at the 5' terminus of the selectable marker gene where a regulatory polynucleotide can be inserted to be operably linked to the selectable marker gene; and a polynucleotide for targeted integration of the vector into the chromosome of a susceptible host. Preferably, the eukaryotic regulatory polynucleotide is a promoter region, and most preferably, a promoter region of pathogenic yeast such as *Candida albicans*. The vector of the invention is preferably transferred to a library of host cells, wherein each host cell contains the vector.

The vector of the invention can be used to identify a eukaryotic regulatory polynucleotide. The method involves inserting genomic DNA of a eukaryotic organism into the vector, wherein the DNA is in operable linkage with the selectable marker gene; transforming a susceptible host with the vector; detecting expression of the selectable marker gene, wherein expression is indicative of operable linkage to a regulatory polynucleotide; and identifying the regulatory polynucleotide.

The vector of the invention also can be used to identify a composition which affects the regulatory DNA (promoter). The method involves incubating the composition to be tested and the promoter, under conditions sufficient to allow the promoter-containing vector of the invention and the composition to interact, and then measuring the effect the composition has on the promoter. The observed effect on the promoter may be either inhibitory or stimulatory.

The method of the invention is useful for identification of promoters from any eukaryote. Particularly preferred eukaryotes are fungal pathogens including, but not limited to, *Candida albicans*, Rhodotorula sp., *Saccharomyces cerevisiae, Blastoschizomyces capitatus, Histoplasma capsulatum, Aspergillus fumigatus, Coccidioides immitis, Paracoccidioides brasiliensis, Blastomyces dermatitidis,* and *Cryptococcus neoformans*.

The invention also features a regulatory polynucleotide (a promoter) isolated using a library of host cells containing the vector of the invention; the promoter is a maltose responsive promoter (MRP), which is induced by maltose and repressed by glucose. MRP is useful for determining whether a polynucleotide encodes a growth-associated polypeptide; the method involves incubating a cell containing the polynucleotide operably linked with the MRP, under conditions which repress the regulatory polynucleotide, and then determining the effect of the expression of the polynucleotide on the growth of the cell.

BRIEF DESCRIPTION OF THE DRAWINGS

Figure 1B:
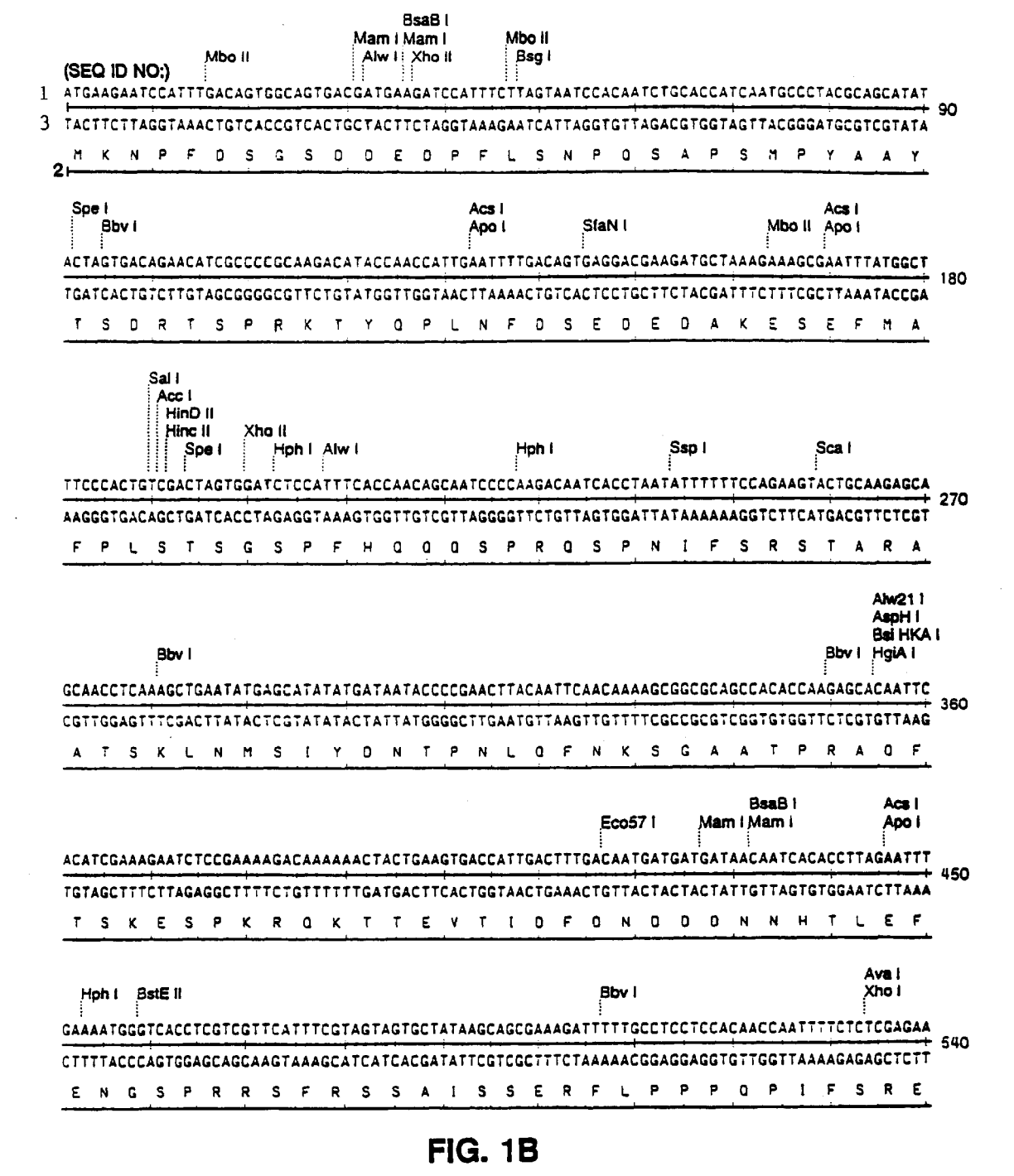
Figure 1C:
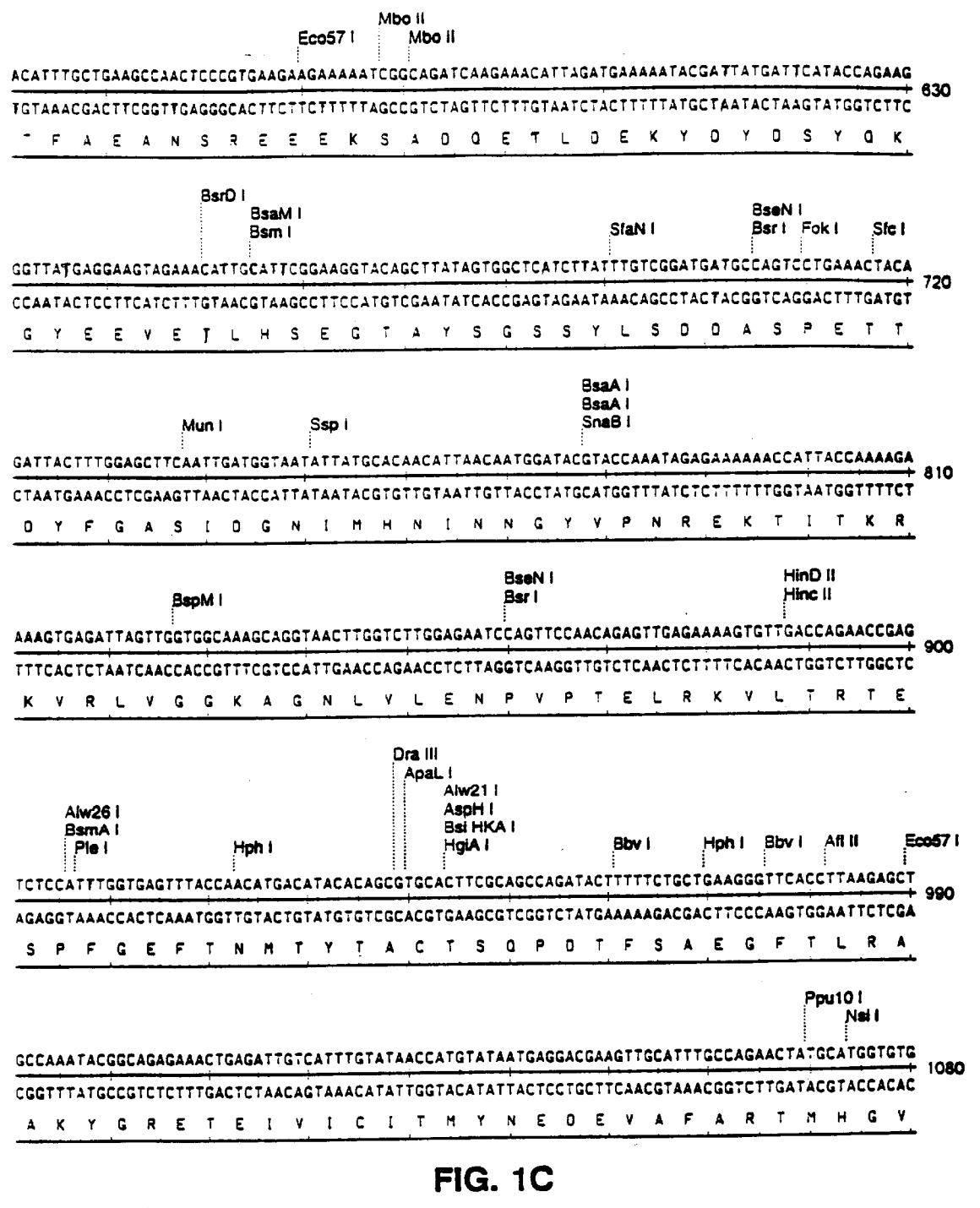
Figure 1F:
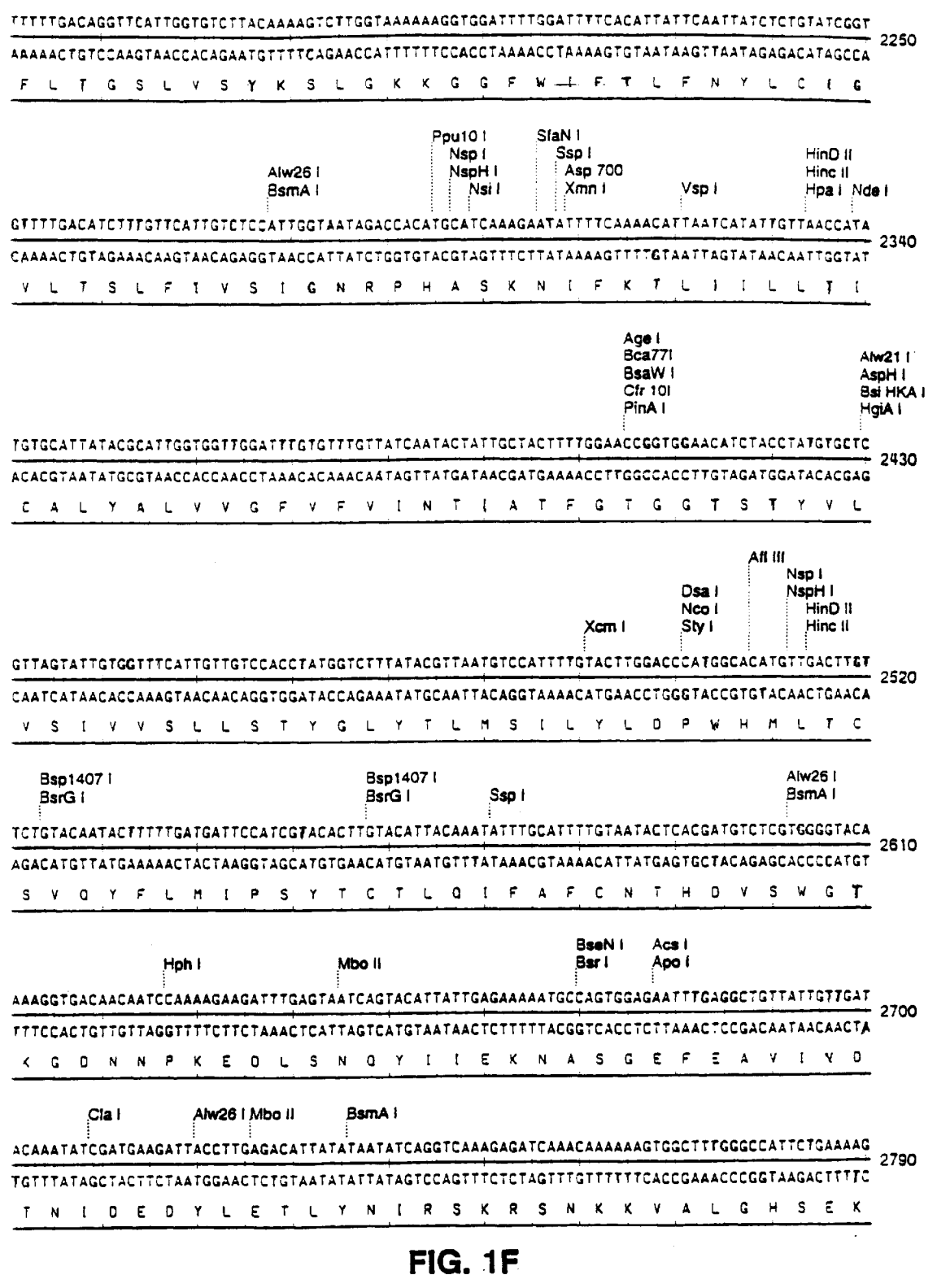

FIGS. 1*b–g* is the nucleotide and deduced amino acid sequence of Chitin Synthase (CHS1) isolated from *Candida albicans* (SEQ ID NO:1, SEQ ID NO:2, and SEQ ID NO:3).

FIGS. 3*a–b* are the nucleotide sequence of the maltose responsive promoter (MRP) from *C. albicans* (SEQ ID NO:4).

FIGS. 7A–D are a demonstration of gene inactivation during infection by MRP. Panels A and B show neutropenic and Panels C and D show immunocompetent mice infected with the indicated strains of *C. albicans*.

DETAILED DESCRIPTION

Figure 1A:
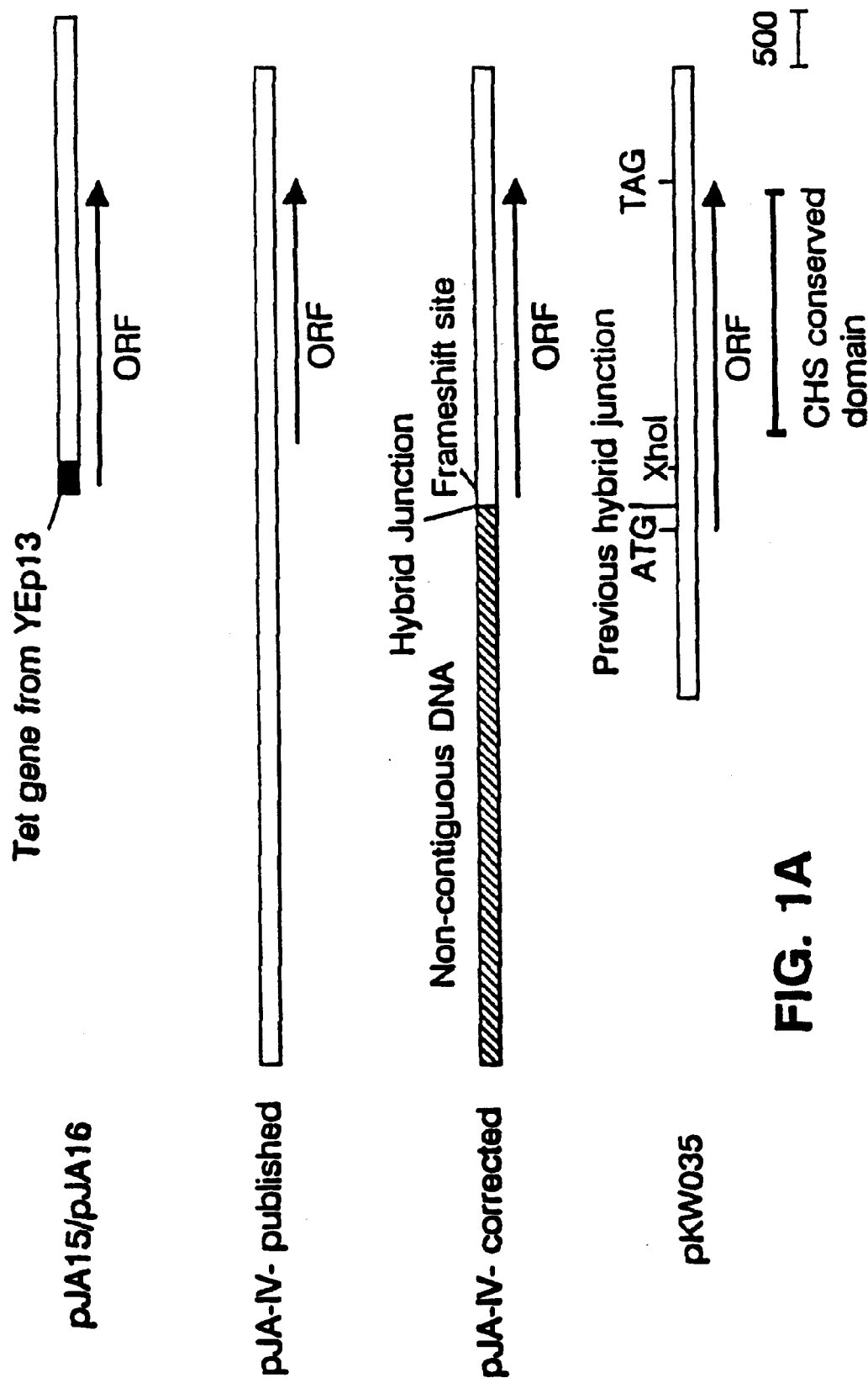
FIG. 1*a* is a comparison of CHS1 clones.

The invention provides genes essential for growth, such as the chitin synthase gene from *Candida albicans* (CaCHS1), as well as vectors for identification of eukaryotic promoters. Preferably, the vector is used for the identification of promoters of fungal pathogens such as *Candida albicans*. The vectors allow identification of promoters and genes under the control of such promoters, many of which are involved in the infection process. A maltose responsive promoter (MRP) is provided as an example of a promoter isolated using the vector of the invention.

Identification of a Yeast Gene Essential for Cell Growth

The invention provides a substantially pure chitin synthase (CHS1) polypeptide. The term "substantially pure" as used herein refers to CHS1 which is substantially free of other proteins, lipids, carbohydrates or other materials with which it is naturally associated. One skilled in the art can purify CHS1 using standard techniques for protein purification. The substantially pure polypeptide will yield a single major band on a non-reducing polyacrylamide gel. The purity of the CHS1 polypeptide can also be determined by amino-terminal amino acid sequence analysis. CHS1 polypeptide includes functional fragments of the polypeptide, provided that the activity of CHS1 remains. Smaller peptides containing the biological activity of CHS1 are also included in the invention.

The invention also provides polynucleotides encoding the CHS1 protein. These polynucleotides include DNA, cDNA and RNA sequences which encode CHS1. It is understood that all polynucleotides encoding all or a portion of CHS1 are also included herein, as long as they encode a polypeptide with CHS1 activity. Such polynucleotides include naturally occurring, synthetic, and manipulated polynucleotides. For example, CHS1 polynucleotide may be subjected to site-directed mutagenesis.

The polynucleotide sequence for CHS1 can be used to produce antisense sequences as well as sequences that are degenerate as a result of the degeneracy of the genetic code; there are 20 natural amino acids, most of which are specified by more than one codon. Therefore, all degenerate nucleotide sequences are included in the invention, provided the amino acid sequence of CHS1 polypeptide encoded by the nucleotide sequence is functionally unchanged.

Specifically disclosed herein is the yeast CHS1 gene, more specifically, the *Candida albicans* CHS1 gene. The sequence is 3084 base pairs long and contains an open reading frame encoding a polypeptide 1027 amino acids in length and having a molecular weight of about 116 kD as determined by reducing SDS-PAGE.

Preferably, the *C. albicans* CHS1 nucleotide sequence is SEQ ID NO:1 and the deduced amino acid sequence is SEQ ID NO:2 (FIGS. 1*b–g*).

The polynucleotide encoding CHS1 includes SEQ ID NO:1 as well as nucleic acid sequences capable of hybridizing to SEQ ID NO:1 under stringent conditions. A complementary sequence may include an antisense nucleotide. When the sequence is RNA, the deoxynucleotides A, G, C, and T of SEQ ID NO:1 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO:2 under stringent physiological conditions.

The CHS1 polypeptide of the invention can be used to produce antibodies which are immunoreactive with or which specifically bind to epitopes of the CHS1 polypeptide. As used herein, the term "epitope" means any antigenic determinant of an antigen to which an antibody to the antigen binds.

Antibodies can be made to the protein of the invention, including monoclonal antibodies, which are made by methods well known in the art (Kohler, et al., *Nature*, 256:495, 1975; *Current Protocols in Molecular Biology*, Ausubel, et al., ed., 1989).

The term "antibody" as used in this invention includes intact molecules as well as fragments thereof, such as Fab, F(ab')2, and Fv which are capable of binding the epitopic determinant. These antibody fragments retain the ability to selectively bind with its antigen or receptor and are defined as follows: (1) Fab, the fragment which contains a monovalent antigen-binding fragment of an antibody molecule can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule. Methods of making these fragments are known in the art. (See for example, Harlow and Lane, Antibodies: A Laboratory Manual, Cold Spring Harbor Laboratory, New York (1988), incorporated herein by reference).

Antibodies which bind to the CHS1 polypeptide of the invention can be prepared using an intact polypeptide or fragments containing small peptides of interest as the immunizing antigen. The polypeptide or a peptide used to immunize an animal can be derived from transcribed/translated cDNA or chemical synthesis, and can be conjugated to a carrier protein, if desired. Such commonly used carriers which can be chemically coupled to the peptide include keyhole limpet hemocyanin (KLH), thyroglobulin, bovine serum albumin (BSA), and tetanus toxoid. The coupled peptide is used to immunize the animal (e.g., a mouse, a rat, or a rabbit).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The invention also provides a method for inhibiting the growth of yeast, by contacting the yeast with a reagent which suppresses CHS1 activity. Preferably the yeast is *C. albicans*.

Where a disease or disorder is associated with the production of CHS1 (e.g., a yeast infection), nucleic acid sequences that interfere with CHS1 expression at the translational level can be used to treat the infection. This approach utilizes, for example, antisense nucleic acids, ribozymes, or triplex agents to block transcription or translation of CHS1 mRNA, either by masking that mRNA with an antisense nucleic acid or triplex agent or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, as the cell will not translate a mRNA that is double-stranded. Antisense oligomers of about 15 nucleotides are preferred, since they are easily synthesized and are less likely to cause problems than larger molecules when introduced into the CHS1-producing cell (e.g., a *Candida albicans*). The use of antisense methods to inhibit the in vitro translation of genes is well known in the art (Marcus-Sakura, *Anal.Biochemn.*, 172:289, 1988).

Use of an oligonucleotide to block transcription is known as the triplex strategy; the oligomer winds around double-helical DNA, forming a three-strand helix. These triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

The reagent used for inhibition of the growth of yeast by suppression of CHS1 activity can be an anti-CHS1 antibody. Addition of such an antibody to a cell or tissue suspected of containing a yeast, such as *C. albicans*, can prevent cell growth by inhibiting cell wall formation.

The invention also provides a method for detecting a yeast cell in a host tissue, for example, which comprises contacting an anti-CHS1 antibody or CHS1 polynucleotide with a cell having a yeast-associated infection and detecting binding to the antibody or hybridizing with the polynucleotide, respectively. The antibody or polynucleotide reactive with CHS1 or DNA encoding CHS1 is labeled with a label which allows detection of binding or hybridization to CHS1 or the DNA. An antibody specific for CHS1 polypeptide or polynucleotide specific for CHS1 polynucleotide may be used to detect the level of CHS1 in biological fluids and tissues of a patient.

The antibodies of the invention can be used, for example, in immunoassays in which they can be utilized in liquid phase or bound to a solid phase carrier.

The anti-CHS1 antibodies of the invention can be bound to a solid support and used to detect the presence of an antigen of the invention. Examples of well-known supports include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

The CHS1 antibodies of the invention can be used in vitro and in vivo to monitor the course of amelioration of a yeast-associated disease in a subject. Thus, for example, by measuring the increase or decrease in the number of cells expressing antigen comprising CHS1 polypeptide of the invention or changes in the concentration of such antigen present in various body fluids, it is possible to determine whether a particular therapeutic regimen aimed at ameliorating the yeast-associated disease is effective. The term "ameliorate" denotes a lessening of the detrimental effect of the yeast-associated disease in the subject receiving therapy.

The CHS1 of the invention is also useful in a screening method to identify compounds or compositions which affect the activity of the protein. To determine whether a compound affects CHS1 activity, the compound is incubated with CHS1 polypeptide, or with a recombinant cell expressing CHS1, under conditions sufficient to allow the components to interact; the effect of the compound on CHS1 activity or expression is then determined.

The increase or decrease of chitin synthase transcription/translation can be measured by adding a radioactive compound to the mixture of components, such as $^{32}$P-ATP or $^{35}$S-Met, and observing radioactive incorporation into CHS1 transcripts or protein, respectively. Alternatively, other labels may be used to determine the effect of a composition on CHS1 transcription/translation. For example, a radioisotope, a fluorescent compound, a bioluminescent compound, a chemiluminescent compound, a metal chelator or an enzyme could be used. Those of ordinary skill in the art will know of other suitable labels or will be able to ascertain such, using routine experimentation. Analysis of the effect of a compound on CHS1 is performed by standard methods in the art, such as Northern blot analysis (to measure gene expression) or SDS-PAGE (to measure protein product), for example. Further, CHS1 enzymatic activity can also be determined, for example, by incorporation of labeled precursor of chitin. Preferably, such precursor is UDP-N-acetylglucoseamine.

Vector for Identification of a Eukaryotic Regulatory Polynucleotide

The vector contains at least one promoterless selectable marker gene and a restriction endonuclease cloning site located at the 5' terminus of the selectable marker. A pool of chromosomal DNA fragments from a eukaryotic organism is inserted at the restriction endonuclease cloning site in operable linkage with the selectable marker polynucleotide. In addition, the vector contains a polynucleotide sequence for targeted integration of the vector into the chromosome of a susceptible host.

As used herein, the term "vector" refers to a nucleic acid molecule capable of transporting another nucleic acid, to which it has been operatively linked, from one genetic environment to another.

The term "regulatory polynucleotide" as used herein preferably refers to a promoter, but can also include enhancer elements. The vectors of the invention contain a promoterless selectable marker gene having a cloning site at the 5' terminus of the gene. The vectors also include a cloning site 5' of the selectable marker gene, which is operably associated with a promoter. The term "operably associated" or "operably linked" refers to functional linkage between the promoter sequence and the controlled nucleic acid sequence; the sequence and promoter are typically covalently joined, preferably by conventional phosphodiester bonds.

The expression vectors of the invention employ a promoterless gene for selection of a promoter sequence. The vectors contain other elements typical of vectors, including an origin of replication, as well as genes which are capable of providing phenotypic selection of transformed cells. The transformed host cells can be grown in the appropriate media and environment, e.g., in fermentors, and cultured according to techniques known in the art to achieve optimal cell growth. The vectors of the present invention can be expressed in vivo in either prokaryotes or eukaryotes. Methods of expressing DNA sequences containing eukaryotic coding sequences in prokaryotes are well known in the art. Biologically functional plasmid DNA vectors used to incorporate DNA sequences of the invention for expression and replication in the host cell are described herein. For example, DNA can be inserted into yeast cells using the vectors of the invention. Various shuttle vectors for the expression of foreign genes in yeast have been reported (Heinemann, et al., *Nature,* 340:205, 1989; Rose, et al., *Gene,* 60:237, 1987).

Host cells include microbial, yeast, and mammalian cells, e.g., prokaryotes and eukaryotes such as yeast, filamentous fungi, and plant and animal cells.

Transformation or transfection with recombinant DNA may be carried out by conventional techniques well known to those skilled in the art. Where the host is prokaryotic, such as *E. coli,* competent cells which are capable of DNA uptake can be prepared from cells harvested after the exponential growth phase and subsequently treated, i.e., by the $CaCl_2$ method using procedures well known in the art.

Where the host cell is eukaryotic, various methods of DNA transfer can be used. These include transfection of DNA by calcium phosphate-precipitates, conventional mechanical procedures such as microinjection, insertion of a plasmid encased in liposomes, spheroplast, electroporation, salt mediated transformation of unicellular organisms, or the use of viral vectors. A library of host cells, wherein each host cell contains a vector according to the description above, is also included in the invention.

Eukaryotic DNA can be cloned into prokaryotes using vectors well known in the art. Because there are many functions in eukaryotic cells which are absent in prokaryotes, (e.g., localization of ATP-generating systems to mitochondria, association of DNA with histone, mitosis and meiosis, and differentiation of cells), the genetic control of such functions must be assessed in a eukaryotic environment. Many eukaryotic vectors, though, are capable of replication in *E. coli,* which is important for amplification of the vector DNA. Thus, vectors preferably contain markers, e.g., LEU 2, HIS 3, URA 3, that can be selected easily in yeast, and in addition, also carry antibiotic resistance markers for use in *E. coli.* The selectable marker gene, which lies immediately downstream from the cloning site, preferably encodes a biosynthetic pathway enzyme of a eukaryote which relies on the enzyme for growth or survival. This biosynthetic pathway gene, once activated, will complement the growth of an auxotrophic host, deficient for the same biosynthetic pathway gene in which it is integrated. Typically, genes encoding amino acid biosynthetic enzymes are utilized, since many strains are available having at least one of these mutations, and transformation events are easily selected by omitting the amino acid from the medium. Examples of markers include but are not limited to URA3, URA3-hisG, LEU2, LYS2, HIS3, HIS4, TRP1, ARG4, $Hgm^R$, and $TUN^R$. Preferably, the vector includes a promoterless URA3 gene. Expression of the *C. albicans* URA 3 gene is required for the infection process, thus creating a strong selection pressure for those sequences cloned upstream of the promoterless URA3 gene that will be induced during the infection process.

The vector of the invention preferably includes a prokaryotic origin of replication or replicon, i.e., a DNA sequence having the ability to direct autonomous replication and maintenance of the recombinant DNA molecule extrachromosomally in a transformed prokaryotic host cell. Such origins of replication are well known in the art; preferred origins of replication are those that are efficient in the host organism, e.g., the preferred host cell, E. coli. For vectors used in E. coli, a preferred origin of replication is ColE1, which is found in pBR322 and a variety of other common plasmids. Also preferred is the p15A origin of replication found on pACYC and its derivatives. The ColE1 and p15A replicon have been extensively utilized in molecular biology, are available on a variety of plasmids, and are described, e.g., in Sambrook, et al., *Molecular Cloning: a Laboratory Manual*, 2nd edition, Cold Spring Harbor Laboratory Press, 1989).

The ColE1 and p15A replicons are particularly preferred for use in the invention because they each have the ability to direct the replication of a plasmid in *E. coli* while the other replicon is present in a second plasmid in the same *E. coli* cell. In other words, ColE1 and p15A are non-interfering replicons that allow the maintenance of two plasmids in the same host (see, for example, Sambrook, et al., supra, at pages 1.3–1.4).

The vector of the invention includes a polylinker multiple cloning site for insertion of selectable marker genes. A sequence of nucleotides adapted for directional ligation, i.e., a polylinker, is a region of the DNA expression vector that (1) operatively links for replication and transport the upstream and downstream translatable DNA sequences, and (2) provides a site for directional ligation of a DNA sequence into the vector. Typically, a directional polylinker is a sequence of nucleotides that defines two or more restriction endonuclease recognition sequences. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. Where the sequence of nucleotides adapted for directional ligation defines numerous restriction sites, it is referred to as a multiple cloning site.

Additionally, the vector may contain a phenotypically selectable marker gene to identify host cells which contain the expression vector. Examples of markers typically used in prokaryotic expression vectors include antibiotic resistance genes for ampicillin (β-lactamases), tetracycline and chloramphenicol (chloramphenicol acetyltransferase).

The vector contains a polynucleotide sequence for targeted integration of the vector into the chromosome of a susceptible host. Targeted integration, as opposed to random integration, results in more stable transformants and avoids position effects or integration into genes required for growth and infection. Preferably, the gene for targeted integration is also a selectable marker, thereby allowing the identification of transformants that contain the vector. Such genes include the adenine biosynthesis (ADE2) gene of *Candida albicans*. A susceptible host is a host having a site recognized by the polynucleotide of the vector for targeted integration.

Promoters identified by the method of the invention can be inducible or constitutive promoters. Inducible promoters can be regulated, for example, by nutrients (e.g., carbon sources, nitrogen sources, and others), drugs (e.g., drug resistance), environmental agents that are specific for the infection process (e.g., serum response), and temperature (e.g., heat shock, cold shock).

Identification of a Eukaryotic Regulatory Polynucleotide

The selection method of the invention utilizes an auxotrophic organism, or an organism that has a mutation in a biosynthetic pathway gene encoding a functional biosynthetic enzyme necessary for the growth of the organism. When a functional or wild-type copy of a biosynthetic pathway gene is inserted into an auxotroph, the expression of the wild-type biosynthetic pathway gene provides the auxotroph with the biosynthetic enzyme required for growth or survival. The process of replacing a missing or non-functional gene of an auxotroph with a functional homologous gene in order to restore the auxotroph's ability to survive within a host cell is called "complementation".

Complementation of the auxotroph, according to the present invention, is accomplished by construction of a vector having a promoterless structural gene encoding a—biosynthetic enzyme, i.e., a selectable marker polynucleotide, as described above. The cloning site for the promoter of interest is at the 5' terminus of the structural gene encoding the biosynthetic enzyme. Consequently, a promoter region operatively linked to any gene or set of genes will control the expression of that gene or genes. In order to be controlled by the promoter, the gene must be positioned downstream from the promoter.

The structural gene encoding a biosynthetic enzyme in the vector of the invention does not contain recognition sequences for regulatory factors to allow transcription of the structural gene. Consequently, the product(s) encoded by the structural gene is not capable of being expressed unless a promoter sequence is inserted into the cloning site 5' to the structural gene.

A second structural gene in the vector allows for targeted insertion and integration into the host cell's chromosomal DNA. Optionally, the vector may contain additional genes, such as those encoding selective markers for selection in bacteria. Typically drug resistance genes such as those described above are used for such selection.

In the method of the invention, total genomic DNA is isolated from the organism, e.g., *Candida albicans*, and then partially enzymatically digested, resulting in a pool of random chromosomal fragments. The vector of the invention is cleaved at the restriction/cloning site, and mixed with the cleaved chromosomal DNA. The chromosomal fragments are ligated into the vector to produce a library, i.e., each vector contains a random chromosomal fragment so that the pool of vectors is representative of the entire organism's genome. The vectors containing the chromosomal fragments are then introduced into the host organism (e.g., an auxotrophic strain or drug resistant strain of *Candida albicans*) by methods well know in the art. For example, the vectors may be introduced by transformation.

After the vector is introduced into the host (e.g., auxotrophic), the vector may integrate into the auxotroph's chromosome by targeted integration. This step can be detected by selection, as described above. For example, the preferred polynucleotide for targeted insertion and integration in *Candida albicans* is the ADE2 gene. The presence of this gene is detectable by growth of the organism on adenine deficient media.

The expression of the biosynthetic enzyme gene, e.g., URA3, whether under constitutive or inducible conditions, is identified by complementation of a host cell strain in which the gene is defective or missing, e.g., URA3-. Only those host cells which can grow in medium lacking the nutritional supplement, e.g., uracil, will be expected to contain a cloned functional promoter sequence.

Identification of a Yeast Regulatory Polynucleotide Capable of Induction and Repression In another aspect, the invention provides an isolated regulatory polynucleotide, the MRP promoter, characterized in that it is induced by maltose and repressed by glucose. MRP of the invention is exemplified by the nucleotide sequence of SEQ ID NO:4 (FIGS. 3a–b), wherein the sequence is 1734 base pairs in length. MRP was isolated from a promoter library based on expression of the Ura3 gene of *C. albicans* as described above. MRP functions bidirectionally, that is, genes flanking MRP both 5' and 3' are controlled by this regulatory polynucleotide.

The MRP of the invention is useful for identifying genes which are essential for cell growth. Thus, the invention provides a method for determining whether a polynucleotide encodes a growth-associated polypeptide, by incubating a cell containing the polynucleotide operably linked with the MRP regulatory polynucleotide, under conditions which repress the regulatory polynucleotide, and determining the effect of the tested polynucleotide on the growth of the cell.

MRP of the invention promotes transcription in the presence of maltose, while the ability of MRP to promote transcription is repressed by glucose. A cell having a polynucleotide of interest operably linked to MRP can be grown on a glucose containing medium to determine whether the polynucleotide of interest is essential for cell growth. MRP is repressed on glucose, thus repressing transcription of the operably linked polynucleotide, therefore, if a cell grown on a glucose containing-medium dies, the polynucleotide is determined to be essential for cell growth.

MRP can be used to induce (maltose) or repress (glucose) expression of a gene operably linked to MRP. It is also envisioned that MRP may be useful for decreasing the expression of a target gene operably linked to MRP, such that the cell containing the MRP-gene of interest is now extremely sensitive to a compound of interest. For example, it may be desirable to increase susceptibility or resistance to a particular therapeutic compound. Similarly, MRP is useful for inducing expression of a gene operatively linked to MRP, by growing a host cell containing a MRP-gene construct on a maltose-containing medium. It may be desirable to elevate gene expression for screening various therapeutic compounds for their effect on the gene product.

The following examples are intended to illustrate but not limit the invention. While they are typical of those that might be used, other procedures known to those skilled in the art may alternatively be used.

EXAMPLES

Example 1
Isolation of Chitin Synthase from *Candida albicans*

Using Southern blotting, the restriction maps for the cloned CHS1 gene contained in pJAIV and the genomic CHS1 locus were produced, however, the maps were found not to match. Additional studies indicated that pJAIV contained two nonadjacent genomic DNA fragments as diagrammed in FIG. 1a. As a consequence, pJAIV lacked the 5' end of CHS1. To clone this region, a plasmid rescue strategy was employed. Plasmid pKW025, which contains a 600 bp KpnI/EcoRI fragment of CHS1, and a 1.4 kb Candida URA3 gene cloned into pSK(-), was cut with ClaI and transformed into *Candida albicans* strain CAI-4. Transformants were examined by Southern blot and strain CAI-4A was identified, containing pKW025 integrated at the CHS1 locus. Genomic DNA was extracted from CA-1-4A and cut with Hind III. Because pKWO25 and the sequenced portion of CHS1 contain no Hind III sites, this digestion yields on a single DNA fragment pKW025 plus the genomic CHS1 locus with flanking regions extending to the 5' and 3' Hind III sites. Ligation was carried out with a low DNA concentration to promote intramolecular ligation events, and the DNA transformed into *E. coli*. Recovered plasmids were screened by PCR to verify that they contained contiguous CHS1 sequence.

Plasmid pKW030 (12 kb total) was identified and contained approximately 2 kb of CHS1 sequence upstream of the XhoI site. A 3.6 kb HindIII/PstI fragment was cloned into the HindIII/PstI sites of pSK(-), forming plasmid pKW032. The 3' region of the gene was derived from plasmid pKW013 (originally derived from pJA-IV). A 3.5 kb BstEII/-NotI fragment was cloned into the BstEII/NotI sites of pKW032, forming plasmid pKW035. pKW035 was cut with various restriction enzymes, and Southern blot analysis also carried out to confirm that the insert was indeed an uninterrupted CHS1 gene whose restriction pattern matched that of the chromosomal CHS1.

The insert was sequenced by standard methods and the nucleotide and deduced amino acid sequence are shown in FIG. 1b–g (SEQ ID NO:1 and 2).

EXAMPLE 2

Construction of Promoter Isolation Vector

The *Candida albicans* URA3 gene was amplified by PCR and a SalI site was inserted next to the ATG. The 3' primer used contained a genomic XbaI site. The SalI/XbaI fragment was cloned in Bluescript KS+ at SalI/XbaI. The *C. albicans* EcoRV genomic fragment containing the ADE2 gene was cloned in the above plasmid at the XhoI site of the Bluescript polylinker.

The Ca URA3 gene was amplified by PCR using the following primers:

```
5' Primer URA3-ATG:   5'-GGAGGA[GTCGAC]ATGACAGTCAACAC-3'   (SEQ ID NO:5)
                             SalI 3' Primer URA3-XbaI:  5'-CGCATTAAAGC[TCTAGA]AGAACCACC-3'    (SEQ ID NO:6)
                                  XbaI (Underlined regions: genomic)
```

The PCR reaction was as follows:
100 ng DNA, 50 pmoles each primer, 2.5 mM dNTP, 2.5 mM Mg $Cl_{21}$, 0.5U Taq Polymerase/100 μl.
Reaction
step 1: 2 min 94° C.
step 2: 1 min 94° C.
step 3: 1 min 57° C.
step 4: 11/2 min 72° C.
step 5: steps 2–4×30 times
step 6: 10 min 72° C.
step 7: Hold 4° C.

Figure 2A:
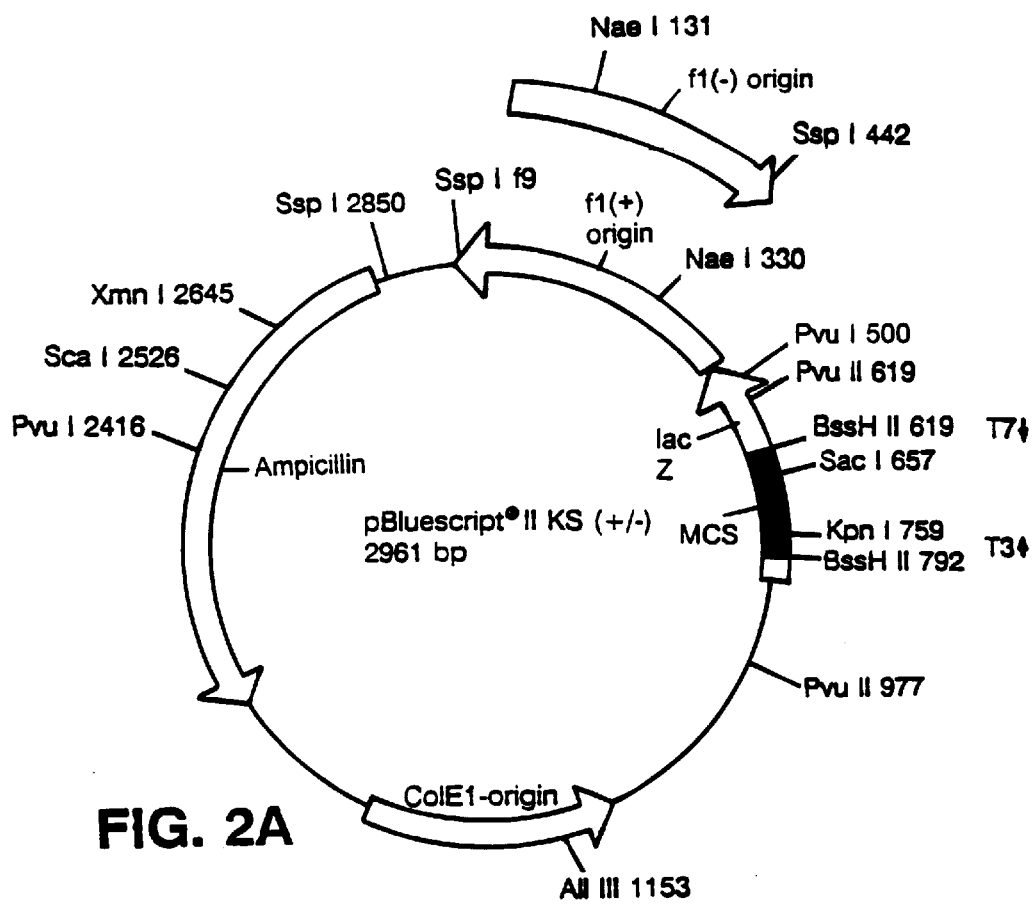
FIG. 2*a* is a restriction map of the vector pBluescripts® II KS (+/−).

For the cloning, 20 μl of the PCR reaction was run on 0.7% low melting agarose gel and the band was purified using the Promega (Madison, Wis.) PCR purification resin. The purified band and 1 µg of Strategene KS+bluescript (FIG. 2a; Stratagene, La Jolla, Calif.) were digested with SalI and XbaI, gel isolated (as above) and eluted in 50 µl water.

The ligation reaction was performed as follows: Ligation (20 µl): 1 µl vector, 10 µl digested PCR band, 2 µl T4 ligase buffer, 1 µl (2 units) T4 ligase (Boehrringer), 6 µl H₂O, over night at room temperature. 10 µl of the ligation was used to transform Strategene XL1 Blue ultra-competent cells selecting for ampicillin resistance. Individual colonies were grown in LB+ampicillin and plasmid DNA was isolated using the Quiagen (Chatsworth, Calif.) spin columns.

Figure 2B:
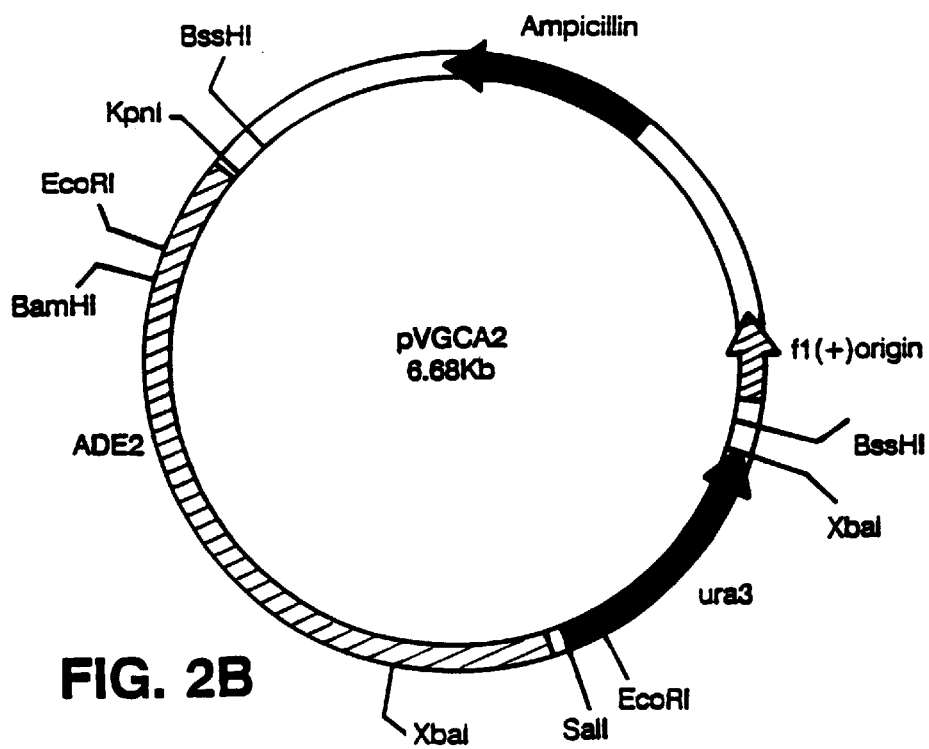
FIG. 2*b* is a restriction map of the vector pVGCA2.

The above plasmid was digested with XhoI, filled in with Klenow for 30 min and dephosporylated. with acid phosphatase for 5 min. The band was gel purified as above. The EcoRV fragment containing the Ca ADE2 gene was cloned into the plasmid using the conditions described above (FIG. 2b).

EXAMPLE 3

Isolation and Characterization of a Maltose Induced/Glucose Repressed Promoter of C. albicans Using the promoter probe vector pVGCAV2 (based on URA3 expression), a library was constructed which inserted 1–2 kb Sau3A fragments (isolated by sucrose gradient centrifugation) upstream (5') of the promoterless URA3 reporter gene into the vector. The vector plasmid was cut with SalI and partially end filled with dT and dC while the insert fragments (Sau3A cut) were partially filled in with dG and dA. These partial fill in reactions left 2 bp overhangs that are compatible for a ligation reaction. The results of the ligation of the library were introduced into E. coli strain DH5A by electroporation, and gave rise to 76,500 independent transformants. Sixteen randomly picked colonies all proved to have inserts indicating the library was sound.

The plasmid library was extracted from E. coli by standard plasmid isolation procedures and cut at the unique BamHI site within the ADE2 gene for targeted integration of the ADE locus of C. albicans strain CaI8 (ade2ura3). The ade2 mutation of CaI8 allows for selection of transformants and the ura3 mutation of CaI8 permits monitoring of expression of the reporter gene URA3. A first pool of 10,000 independent CaI8 transformants was tested for regulated URA3 expression. The CaI8 transformants were plated on Synthetic Dextrose [glucose medium (2% glucose (w/v) and yeast nitrogen base without amino acids at 6.7 g/L (Difco)) without uridine] to determine the frequency of transformants expressing the URA3 gene constitutively. Fourteen per cent of the Candida CaI8 transformants expressed varying levels of the URA3 gene as determined by the ability to form colonies on a medium lacking uridine supplementation. The pool was then treated with the compound 5-FOA to remove these transformants expressing the URA3 gene constitutively (transformants expressing URA3 convert 5-Fluoroorotic acid to a toxic compound and thus can be eliminated from the pool). To isolate promoters responding to specific carbon sources, aliquots of the pool were grown on synthetic glucose medium supplemented with uridine and replicated to synthetic maltose medium without uridine. Candida transformants able to produce colonies on the unsupplemented maltose medium putatively contained a maltose inducible promoter. Four strains (MRP-2, MRP-5, MRP-6, MRP-7) were shown to show maltose dependent growth that was repressed upon the addition of glucose.

Chromosomal DNA was extracted from the Candida CaI8 transformants exhibiting maltose dependent growth (MRP strains) and digested with the restriction enzyme BamHI to "release the MRP clones." The "released" plasmids were ligated and introduced into E. coli by transformation. These E. coli transformants were used as a source of plasmid DNA for dideoxy/chain termination sequencing. Initial sequencing data using a primer to URA3 sequences just downstream of the insert (3') indicated all the MRP strains contained the same insert. Sequencing data obtained using a primer to ADE2 sequences (5' to the insert DNA with respect to URA3 transcription indicated the clone contained part of a maltase gene and regulatory sequences (FIGS. 3a–b, SEQ ID NO:4). The entire sequence of the clone was assembled and the portion of the maltase ORF contained on the insert was shown to be approximately 70% sequence identical to a previously cloned promoter of C. albicans maltase (CAMAL2) (Geber, et al., J. Bacteriology, 174:6992, 1992).

EXAMPLE 4

Identification of Genes Essential for Yeast Cell Growth

This experiment used the MRP promoter as a gene disruption tool, and the C. albicans CHS1 gene. A strain was constructed and designated KWC340, in which CHS1 expression is regulated by the carbon source present in the growth medium. Transcription of CHS1 was induced by maltose and repressed by glucose. In maltose containing medium, KWC340 grows at the same rate as a wild-type strain. When KWC340 is transferred to glucose-containing medium, cells stop growing and eventually die. Three generations after transfer to glucose, short chains of cells grow but fail to separate. Ten generations after transfer, growth has stopped. Long chains and clumps of cells are seen; a large percentage of the cells are anucleate or multinucleate, indicating a defect in nuclear segregation. Viability is reduced approximately 500-fold relative to a control culture, as judged by plating efficiency.

Figure 4:
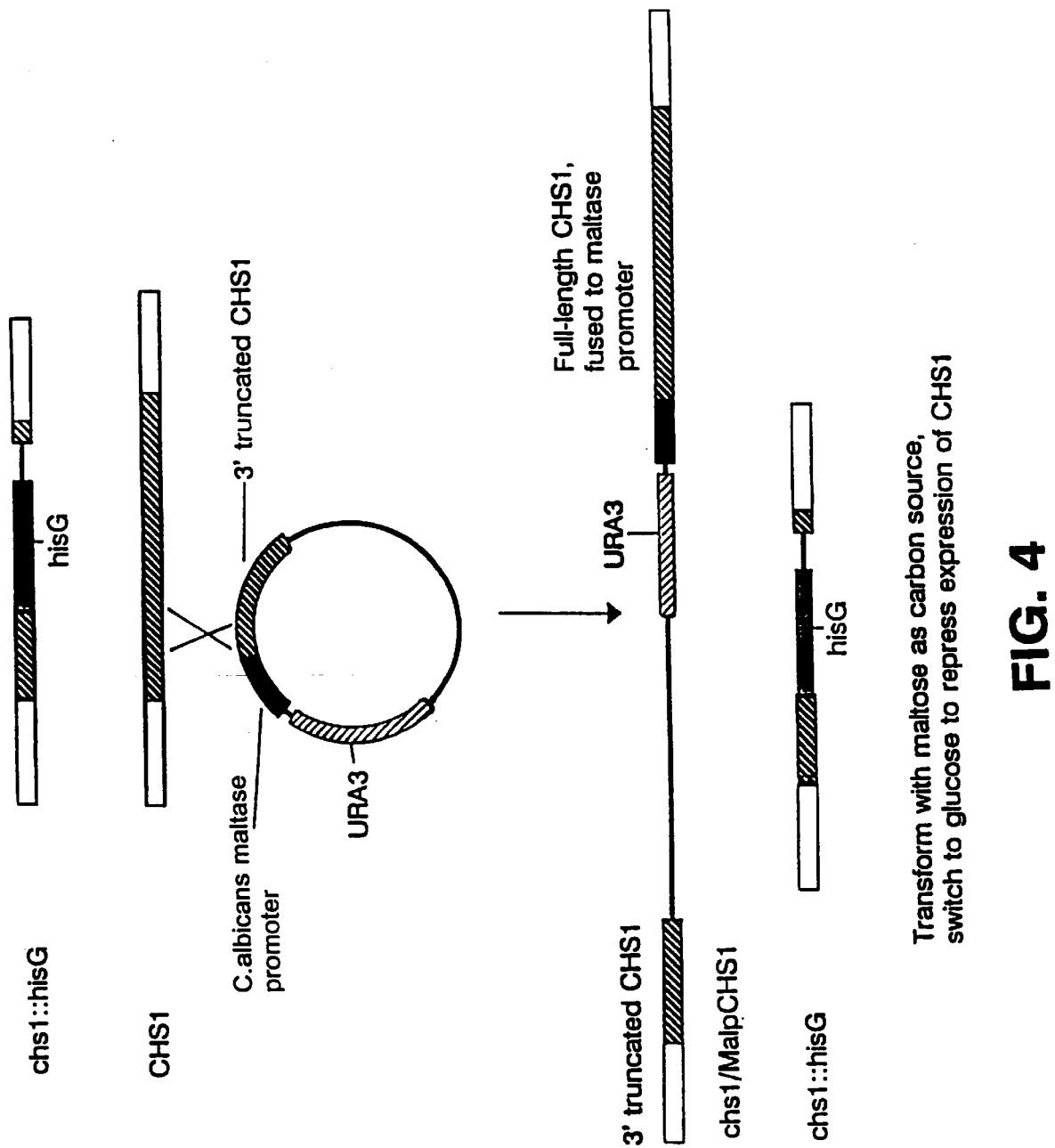
FIG. 4 is a schematic illustration showing regulated expression of CHS1 operatively linked to MRP.

As a first step in constructing a strain in which the sole functional CHS1 gene was under the control of the MRP fragment, a vector was constructed in pKS termed KWO44 with the following features (see FIGS. 4–6):

(a) the plasmid contained URA3 for selection of transformants in the Ura-strains CaI4 (CHS1/CHS1) and 167b (CHS1/chs1::hisG)

Figure 5:
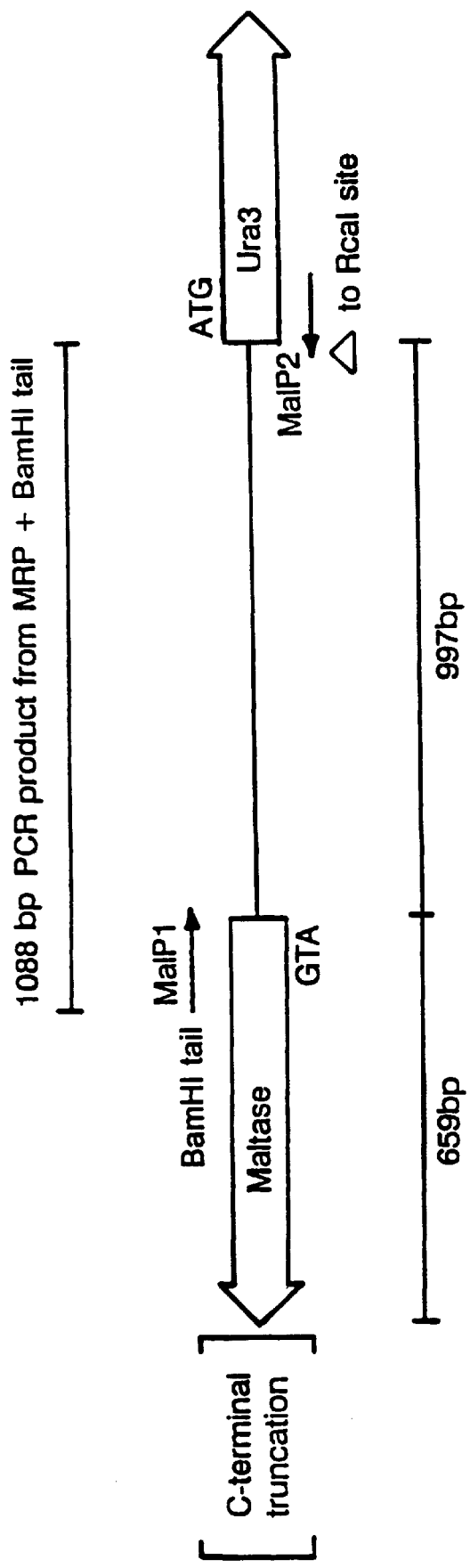
FIG. 5 is a schematic illustration showing the bidirectional regulation capability of MRP.
Figure 6:
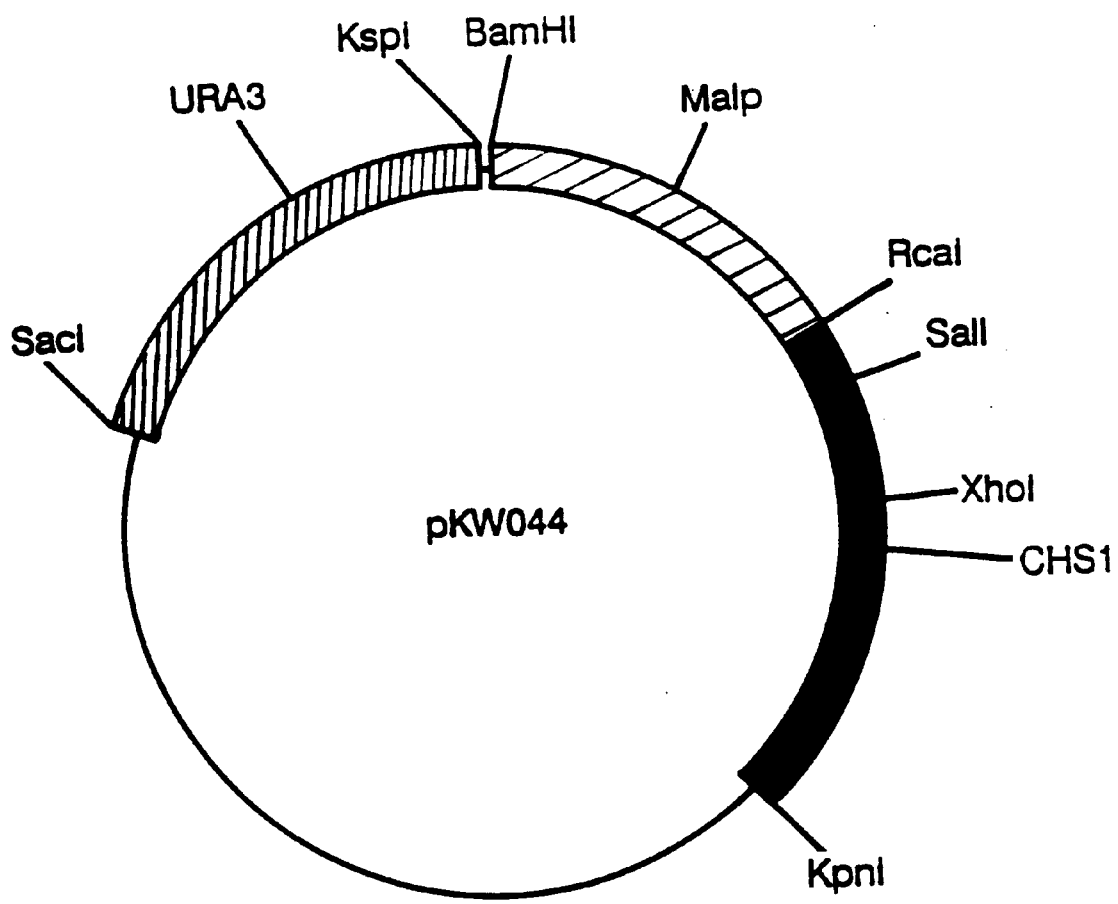
FIG. 6 is a restriction map of the pKW044 vector including the CHS1 gene.

(b) a 1088 bp PCR fragment of the MRP sequence (see attached FIG. 5 showing sites of PCR primers)

(c) 1479 bp of the C. albicans CHS1 N-terminus that contains a unique XhoI site to target the transformation/-integration event.

This construct fuses the ATG initiation codon of the CHS1 gene at the same position as the URA3 gene (original reporter gene used to isolate the MRP clone) with respect to the MRP fragment. Integration of this construct at the remaining wild-type CHS1 allele in strain 167b places the sole functional CHS1 gene under the control of the transcriptional control of the MRP fragment. After transformation this type of integrants were recovered as confirmed by Southern analysis. These integrants grew well on maltose containing medium (inducing conditions) but died when replicated to glucose containing medium.

When injected into mice, the MRP-CHS1 integrants were avirulent;the symptoms diagnostic of candidiasis were not observed, and the kidneys from the mice were sterile. Thus CHS1 is essential for growth in vitro and in vivo. Briefly, ICR 4-week-old male mice (Harlan Sprague Dawley) were housed five per cage; food and water were given ad libitum according to the National Institutes of Health guidelines for the ethical treatment of animals. Strains of *C. albicans* were grown in SM medium [2% maltose, 0.7% yeast nitrogen base without amino acids (Difco Laboratories, Detroit, Mich.)] to a density of $10^7$ cells/ml. Cells were harvested, washed, resuspended in sterile water, and injected into mice ($10^6$ cells/immunocompetent mouse, $10^4$ cells/neutropenic mouse) via the lateral tail veins. For each strain of *C. albicans*, five mice were infected. Cages were checked three times daily for mice dead or moribund (exhibiting severe lethargy, vertigo, and ruffled fur) mice. Moribund mice were euthenized by cervical dislocation and necropsied. The left and right kidneys were removed and examined for colonization by *C. albicans*. In experiments using neutropenic mice, cyclophosphamide was administered (150 mg/kg) by intraperitoneal injection 96 and 24 hours prior to infection. Injections were repeated every three days for the duration of the experiment. Neutropenia was verified by comparing the percentage of neutrophils to total number of leukocytes before and after injection with cyclophosphamide.

FIG. 7, panels A–D, shows the results of the in vivo experiment. Neutropenic (panels A & B) and immunocompetent (panels C & D) mice were infected with the indicated strains of *C. albicans:* clinical isolate (strain SC5314, , panels A & C); MRP::URA3 (strain MRP2, a derivative of SC5314 containing one copy of URA3 which is regulated by MRP, □, panels A & C); MRP::CHS1 (strain KWC340, a derivative of SC5314 containing one copy of CHS1 which is regulated by MRP, ▲, panels B & D); and CHS1/MRP::CHS1 (strain KWC352, a derivative of SC5314 containing two copies of CHS1; one regulated by MRP, the other by the CHS1 promoter, ○, panels B & D).

In conclusion, these results show the MRP clone controls the expression of two non cognate genes (CHS1 and URA3) in a regulated manner and demonstrate the utility of the MRP sequence as a genetic tool in *C. albicans* for target validation (determination of gene essentiallity).

Although the invention has been described with reference to the presently preferred embodiment, it should be understood that various modifications can be made without departing from the spirit of the invention. Accordingly, the invention is limited only by the following claims.

---

What is claimed is:

1. An isolated regulatory polynucleotide comprising the sequence of SEQ ID NO:4, characterized in that it is induced by maltose and repressed by glucose.

2. The regulatory polynucleotide of claim 1, wherein the regulatory polynucleotide is derived from a yeast cell.

3. A method for determining whether a test polynucleotide encodes a growth-associated polypeptide, said method comprising:

a) incubating a fungal cell comprising the test polynucleotide operably linked with the regulatory polynucleotide of claim 1, under conditions which repress the regulatory polynucleotide; and b) determining the effect of the test polynucleotide on the growth of the cell.

4. The method of claim 3, wherein the effect is inhibition of cell growth.

5. An isolated regulatory polynucleotide of claim 1, further comprising a coding sequence operably linked to the isolated regulatory polynucleotide.

6. A vector comprising an isolated regulatory polynucleotide of claim 1.

7. A host cell comprising an isolated regulatory polynucleotide of claim 1.

8. A host cell comprising a vector of claim 6.

* * * * *